United States Patent
Song et al.

(10) Patent No.: US 10,309,969 B2
(45) Date of Patent: Jun. 4, 2019

(54) PROTEIN COMBINATION-BASED FV LIBRARY, AND PREPARATION METHOD THEREFOR

(71) Applicant: AbTLAS CO., LTD., Gangwon-do (KR)

(72) Inventors: Byeong Doo Song, Gangwon-do (KR); Jee Sun Yun, Gangwon-do (KR); Song Yi Lee, Gangwon-do (KR); Hye In Kim, Gangwon-do (KR); Hyo Jung Choi, Gangwon-do (KR); Jong Rip Choi, Gangwon-do (KR)

(73) Assignee: AbTLAS CO., LTD. (KR)

( * ) Notice: Subject to any disclaimer, the term of this patent is extended or adjusted under 35 U.S.C. 154(b) by 442 days.

(21) Appl. No.: 14/760,996

(22) PCT Filed: Jan. 24, 2014

(86) PCT No.: PCT/KR2014/000697
§ 371 (c)(1),
(2) Date: Jul. 14, 2015

(87) PCT Pub. No.: WO2014/116051
PCT Pub. Date: Jul. 31, 2014

(65) Prior Publication Data
US 2016/0025740 A1    Jan. 28, 2016

Related U.S. Application Data

(60) Provisional application No. 61/756,066, filed on Jan. 24, 2013.

(51) Int. Cl.
*G01N 33/68* (2006.01)
*C07K 16/00* (2006.01)
*C07K 16/46* (2006.01)

(52) U.S. Cl.
CPC ......... *G01N 33/6845* (2013.01); *C07K 16/00* (2013.01); *C07K 16/46* (2013.01); *G01N 33/6857* (2013.01); *C07K 2317/56* (2013.01); *C07K 2317/565* (2013.01); *C07K 2317/62* (2013.01)

(58) Field of Classification Search
None
See application file for complete search history.

(56) References Cited

U.S. PATENT DOCUMENTS

| | | | | |
|---|---|---|---|---|
| 5,565,332 | A | * | 10/1996 | Hoogenboom ........ C07K 16/18 435/235.1 |
| 8,101,553 | B1 | | 1/2012 | Kurosawa et al. |
| 2012/0058906 | A1 | | 3/2012 | Smider et al. |
| 2012/0129702 | A1 | | 5/2012 | Luo et al. |

FOREIGN PATENT DOCUMENTS

| | | |
|---|---|---|
| CN | 1912111 A | 2/2007 |
| CN | 102199593 A | 9/2011 |
| CN | 102618940 A | 8/2012 |
| JP | 2004501379 A | 1/2004 |
| JP | 2007533304 A | 11/2007 |
| JP | 2008505642 A | 2/2008 |
| JP | 2009510998 A | 3/2009 |
| JP | 2010522566 A | 7/2010 |
| KR | 10-0458083 B1 | 11/2004 |
| KR | 10-2006-0097143 A | 9/2006 |
| KR | 10-2010-0015902 A | 2/2010 |
| WO | 0162907 A1 | 8/2001 |
| WO | WO 2001098534 A2 | 12/2001 |
| WO | 03018785 A1 | 3/2003 |
| WO | WO 2005042774 A2 | 5/2005 |
| WO | WO 2005069970 A2 | 8/2005 |
| WO | WO 2006023144 A2 | 3/2006 |
| WO | WO 2007018853 A2 | 2/2007 |
| WO | WO 2008118970 A2 | 10/2008 |
| WO | WO 2011062862 A1 | 5/2011 |
| WO | 2012125733 A2 | 9/2012 |

OTHER PUBLICATIONS

Knappik, A., et al., "Fully Synthetic Human Combinatorial Antibody Libraries (HuCAL) Based on Modular Consensus Frameworks and CDRs Randomized with Trinucleotides", "Journal of Molecular Biology", Feb. 11, 2000, pp. 57-86, vol. 296, No. 1.
Urlinger, S., et al., "A New Antibody Library Concept", "AB Engineering Congress, San Diego", Dec. 1, 2011, Publisher: https://www.morphosys.com/sites/default/files/downloads/111205_mor_ylanthia_ab_engineering_final.pdf.
Zhu, Z., et al., "Remodeling Domain Interfaces to Enhance Heterdimer Formation", "Protein Science", Jan. 22, 1997, pp. 781-788, vol. 6, No. 4.
Written Opinion dated May 2, 2014 in PCT/KR2014/000697 by the International Searching Authority.
English Translation of the Written Opinion dated May 2, 2014 in PCT/KR2014/000697 by the International Searching Authority.
Glanville, J., et al., "Precise Determination of the Diversity of a Combinatorial Antibody Library Gives Insight into the Human Immunoglobulin Repertoire", "Proceedings of the National Academy of Sciences of the United States of America", Dec. 1, 2009, pp. 20216-20221, vol. 106, No. 48.

(Continued)

*Primary Examiner* — Christopher M Gross
(74) *Attorney, Agent, or Firm* — Jones Day

(57) ABSTRACT

The present invention relates to a method for constructing an Fv library based on a combination of proteins, a method of screening a desired antibody using the constructed Fv library, an Fv antibody screened by the screening method, and an Fv library constructed by the Fv library construction method. The Fv library of the present invention is based on a combination of proteins so that members thereof can be individually analyzed for their function. Moreover, the Fv library enables a desired Fv antibody to be screened without needing a target antigen preparation. In addition, the protein combination based Fv library makes it possible to significantly reduce the number of protein purification processes to thereby reduce costs and time, compared to conventional DNA-based libraries.

17 Claims, 27 Drawing Sheets

Specification includes a Sequence Listing.

(56) References Cited

OTHER PUBLICATIONS

Wang, X., et al., "Antibody Engineering Using Phage Display with a Coiled-Coil Heterodimeric Fv Antibody Fragment", "PLoS One", Apr. 28, 2011, pp. 1-8, vol. 6, No. 4.

Xu, L., et al., "Combinatorial Surrobody Libraries", "Proceedings of the National Academy of Sciences of the United States of America", Aug. 5, 2008, pp. 10756-10761, vol. 105, No. 31.

Yin, C., et al., "Construction of a Fully Synthetic Human scFv Antibody Library with CDR3 Regions Randomized by a Split-Mix-Split Method and Its Application", "The Journal of Biochemistry", Aug. 19, 2008, pp. 591-598, vol. 144, No. 5.

Arndt, K., et al., "A Heterodimeric Coiled-coil Peptide Pair Selected in Vivo from a Designed Library-versus-Library Ensemble", "J. Mol. Biol.", 2000, pp. 627-639, vol. 295.

Arndt, K., et al., "Helix-stabilized Fv (hsFv) Antibody Fragments: Substituting the Constant Domains of a Fab Fragment for a Heterodimeric Coiled-coil Domain", "J. Mol. Biol.", 2001, pp. 221-228, vol. 312.

Arndt, K., et al., "Comparison of in Vivo Selection and Rational Design and Rational Design", "Structure", Sep. 2002, pp. 12351248, vol. 10.

Fernandez-Rodriguez, J., et al., "Induced heterodimerization and purification of two target proteins by a synthetic coiled-coil tag", "Protein Science", Jan. 30, 2012, pp. 511-519, vol. 21.

Litowski, J., et al., "Designing heterodimeric two-stranded alpha-helical coiled-coils: the effect of chain length on protein folding, stability and specificity", "J. Peptide Res.", 2001, pp. 477-492, vol. 58.

Litowski, J., et al., "Designing Heterodimeric Two-stranded alpha-Helical Coiled-coils", "The Journal of Biological Chemistry", Oct. 4, 2002, pp. 37272-37279, vol. 277, No. 40.

Mao, H., et al., "Spatially addressed combinatorial protein libraries for recombinant antibody discovery and optimization", "Nature Biotechnology", Oct. 24, 2010, pp. 1195-1202, vol. 28, No. 11.

Notice of Allowance issued in Korean Patent Application No. 10-2015-7020295 dated Jul. 13, 2017 by the Korean Intellectual Property Office.

English Translation of Notice of Allowance issued in Korean Patent Application No. 10-2015-7020295 dated Jul. 13, 2017 by the Korean Intellectual Property Office.

* cited by examiner

FIG. 6

Comparison of fusion with non-fusion system

| No. | Mutants | Molecular weight (kDa) | | Purification yields (mg/L) | | Increased folds |
|---|---|---|---|---|---|---|
| | | Non-fusion | Fusion | Non-fusion | Fusion | Fusion/non-fusion |
| 1 | VH-wt | 14.7 | 14.7 | 0.2 | 1.3 | 6.5 |
| 2 | VL-wt | 12.9 | 12.9 | 10 | 33.3 | 3.3 |

Production yields of VH and VL mutants by flag tagged sortase fusion system

| No. | Mutants | Molecular weight (kDa) | | | Purification yields (mg/L) | | | Increased folds | | |
|---|---|---|---|---|---|---|---|---|---|---|
| | | No tag | short Flag tag (N-term) | short Flag tag (N-term & C-term) | No tag | short Flag tag (N-term) | short Flag tag (N-term & C-term) | No tag/ No tag | Flag tag(N-)/ No tag | Flag tag(N-, C-)/ No tag |
| by fusion system | | | | | | | | | | |
| 1 | VH wt | 14.7 | - | - | 1.3 | - | - | 1 | | |
| with coiled coil domains | | | | | | | | | | |
| 2 | VH-Winzip A1 | 21.5 | 22 | 22.5 | 0.3 | 1.4 | 1.5 | 1 | 5 | 5 |
| 3 | VH-Winzip A2 | 21.5 | 22 | 22.6 | 1.7 | 3.2 | 10.1 | 1 | 2 | 6 |
| 4 | VH-VelA1 | 21.4 | 21.4 | 22 | 0.6 | 2.6 | 17.7 | 1 | 4 | 30 |
| 5 | VH-VSAL E5 | 21.1 | 21.7 | 22.2 | 3.4 | 8.5 | 6.3 | 1 | 3 | 2 |
| 6 | VH-VSAL E3 ox | 22.8 | 23.4 | 23.9 | 0.5 | 10.3 | 27.7 | 1 | 21 | 55 |
| 7 | VH-EE1234L | 21.6 | 22.1 | 22.6 | 1.9 | 6.8 | 4.3 | 1 | 4 | 2 |
| 8 | VH-MaX | 20.2 | 20.7 | 21.2 | 1.2 | 3.8 | 8.3 | 1 | 3 | 7 |
| 9 | VH-JAALE3 | 19.9 | 20.5 | 21 | - | 9 | 13.8 | 1 | | |
| 10 | VL wt | 12.9 | - | - | 33.3 | - | - | 1 | | |
| 11 | VL-Winzip B1 | 20 | - | - | 22.7 | - | - | | | |
| 12 | VL-Winzip B2 | 20.1 | - | - | 20 | - | - | | | |
| 13 | VL-VelB1 | 20 | - | - | 25 | - | - | | | |
| 14 | VL-VSAL K5 | 19.9 | - | - | 2.4 | - | - | | | |
| 15 | VL-VSAL K3 ox | 21.7 | - | - | 3.3 | - | - | | | |
| 16 | VL-C-Myc | 20 | - | - | 33 | - | - | | | |
| 17 | VL-RR1234L | 18.7 | - | - | 1.7 | - | - | | | |
| 18 | VL-JAALE3 | 18.6 | - | - | 19.3 | - | - | | | |
| with cysteine mutants | | | | | | | | | | |
| 19 | VH-G44C | 14.3 | - | - | 1.3 | 7 | 18.3 | 1 | 5 | 14 |
| 20 | VH-Q105C | 14.2 | - | - | 1 | - | - | | | |
| 21 | VL-A43C | 12.5 | - | - | 2.3 | - | - | | | |
| 22 | VL-Q100C | 12.6 | - | - | 9.3 | - | - | | | |
| 23 | VLK3-Q100C | 13.6 | - | - | 12.4 | - | - | | | |

| | | | | | | | | | | | | | |
|---|---|---|---|---|---|---|---|---|---|---|---|---|---|
| L1 | 16.0 | L28 | 6.8 | L55 | 8.2 | L82 | 2.3 | H1 | 2.2 | H30 | 2.2 | H73 | 2.6 | H101 | 1.1 |
| L2 | 5.6 | L29 | 85.6 | L56 | 14.3 | L83 | 24.0 | H2 | 4.4 | H31 | 1.0 | H74 | 3.3 | H102 | 2.7 |
| L3 | 4.0 | L30 | 10.0 | L57 | 13.5 | L84 | 2.3 | H3 | 1.5 | H32 | 2.5 | H75 | 2.8 | H103 | 1.7 |
| L4 | 2.7 | L31 | 16.0 | L58 | 5.5 | L85 | 13.0 | H4 | 2.6 | H33 | 1.0 | H76 | 2.2 | H104 | 2.0 |
| L5 | 5.7 | L32 | | L59 | 4.1 | L86 | 7.0 | H5 | 2.9 | H35 | 1.0 | H77 | 1.2 | H105 | 1.2 |
| L6 | 7.8 | L33 | 48.0 | L60 | 12.7 | L87 | 10.2 | H6 | 1.7 | H36 | 1.1 | H78 | 2.0 | H107 | 1.0 |
| L7 | 9.2 | L34 | 9.8 | L61 | 28.3 | L88 | 7.0 | H7 | 1.5 | H37 | 2.3 | H79 | 2.6 | H108 | 1.5 |
| L8 | 9.2 | L35 | 39.2 | L62 | 21.4 | L89 | 14.0 | H8 | 1.7 | H38 | 1.0 | H81 | 2.2 | H109 | 3.4 |
| L9 | 9.6 | L36 | 30.0 | L63 | 17.1 | L90 | 25.0 | H9 | 1.0 | H39 | 1.0 | H82 | 3.7 | H110 | 1.0 |
| L10 | 1.9 | L37 | 31.9 | L64 | 8.4 | L91 | 25.0 | H11 | 3.9 | H40 | 1.0 | H83 | 2.8 | H113 | 2.1 |
| L11 | 8.2 | L38 | 9.8 | L65 | 28.3 | L92 | 7.0 | H12 | 1.4 | H41 | 1.0 | H84 | 2.8 | H114 | 1.7 |
| L12 | | L39 | 20.0 | L66 | 2.3 | L93 | 15.0 | H14 | 3.0 | H49 | 3.3 | H85 | 3.9 | H115 | 1.3 |
| L13 | 11.3 | L40 | 4.2 | L67 | 29.8 | L94 | 4.8 | H15 | 2.3 | H50 | 4.6 | H86 | 2.8 | H116 | 2.1 |
| L14 | | L41 | 62.3 | L68 | 12.7 | L95 | 3.8 | H16 | 1.5 | H51 | 2.2 | H87 | 2.1 | H117 | 2.0 |
| L15 | 30.5 | L42 | 19.7 | L69 | 37.7 | L96 | | H17 | 3.3 | H52 | 2.9 | H88 | 2.8 | H118 | 2.2 |
| L16 | 3.3 | L43 | 17.1 | L70 | 9.3 | L97 | 23.0 | H18 | 2.3 | H54 | 2.2 | H89 | 2.3 | H119 | 2.2 |
| L17 | 38.6 | L44 | 29.3 | L71 | 24.0 | L98 | 20.0 | H19 | 4.4 | H55 | 1.1 | H90 | 3.4 | H120 | 2.6 |
| L18 | | L45 | 9.3 | L72 | 9.7 | L99 | 20.0 | H20 | 5.0 | H56 | 1.0 | H91 | 3.9 | H121 | 2.8 |
| L19 | 8.5 | L46 | 11.2 | L73 | 27.4 | L100 | 3.7 | H21 | 2.3 | H57 | 1.1 | H92 | 2.2 | H122 | 2.3 |
| L20 | 5.9 | L47 | 25.4 | L74 | 16.0 | L101 | 21.0 | H22 | 3.1 | H58 | 1.1 | H93 | 3.3 | | |
| L21 | 2.3 | L48 | | L75 | 28.0 | L102 | 20.0 | H23 | 7.2 | H63 | 1.4 | H94 | 2.4 | | |
| L22 | 4.0 | L49 | 20.0 | L76 | 6.0 | L103 | 34.4 | H24 | 2.6 | H66 | 3.0 | H95 | 1.4 | | |
| L23 | 47.5 | L50 | 44.6 | L77 | 9.3 | L104 | 15.0 | H25 | 2.4 | H67 | 2.7 | H96 | 1.8 | | |
| L24 | 5.9 | L51 | 20.0 | L78 | 5.6 | L105 | 17.0 | H26 | 4.6 | H69 | 2.6 | H97 | 2.0 | | |
| L25 | 9.9 | L52 | 2.2 | L79 | 12.1 | L106 | 3.0 | H27 | 8.3 | H70 | 4.4 | H98 | 1.3 | | |
| L26 | 16.2 | L53 | 16.6 | L80 | 14.4 | L107 | 12.0 | H28 | 2.0 | H71 | 3.4 | H99 | 2.0 | | |
| L27 | 22.8 | L54 | 2.4 | L81 | 14.9 | L108 | 6.3 | H29 | 1.7 | H72 | 2.8 | H100 | 2.2 | | |

FIG. 23
Screening of individual Fvs for interaction with ten mixed antigens by Alpha Screen Analysis
Screening of interaction of selected Fvs with ten individual antigens by Alpha Screen Analysis
Biochemical characterization & Cell based assay of selected Fvs
| No. | Antigen |
|---|---|
| 1 | FC |
| 2 | CTLA4-FC |
| 3 | 41BB-FC |
| 4 | TRAIL R1-FC |
| 5 | cMET-FC |
| 6 | TRAIL R2-FC |
| 7 | CD40-FC |
| 8 | FZD7-FC |
| 9 | CD30-FC |
| 10 | IL17R-FC |
| 11 | CSF1R-FC |

Incubation FVs(myc tagged) with Biotinylated antigens-Fc -> Incubation with anti-myc-conjugated Acceptor beads -> Incubation with Streptavidin-coated Donor -> Detection Coating of Anti-myc -> Incubation with FVs(myc tagged)-> Incubation with Antigens-Fc -> Incubation with Anti-huFc HRP-> Detection

- huFC: Antigen-Fc-> Anti-huFc-HRP -> Detection

- Myc: Antigen-Fc-> FVs(myc tagged)-> Anti-myc-> Anti-mouse-HRP-> Detection

Incubation FVs(myc tagged) with Biotinylated antigens-Fc -> Incubation with anti-myc-conjugated Acceptor beads -> Incubation with Streptavidin-coated Donor -> Detection

SEQUENCE LISTING

```
<160> NUMBER OF SEQ ID NOS: 46

<210> SEQ ID NO 1
<211> LENGTH: 50
<212> TYPE: DNA
<213> ORGANISM: Artificial
<220> FEATURE:
<223> OTHER INFORMATION: primer

<400> SEQUENCE: 1
ccgtggccca ggcggccgca agcagcggcc tgaacgacat cttcgaggcc            50
```

<210> SEQ ID NO 2
<211> LENGTH: 43
<212> TYPE: DNA
<213> ORGANISM: Artificial
<220> FEATURE:
<223> OTHER INFORMATION: primer

<400> SEQUENCE: 2
atgtcatatg gcaagcagcg gcctgaacga catcttcgag gcc         43

<210> SEQ ID NO 3
<211> LENGTH: 45
<212> TYPE: DNA
<213> ORGANISM: Artificial
<220> FEATURE:
<223> OTHER INFORMATION: primer

<400> SEQUENCE: 3
ctgcatttcg tgccactcga tcttctgggc ctcgaagatg tcgtt       45

<210> SEQ ID NO 4
<211> LENGTH: 39
<212> TYPE: DNA
<213> ORGANISM: Artificial
<220> FEATURE:
<223> OTHER INFORMATION: primer

<400> SEQUENCE: 4
atcgagtggc acgaaatgca ggctaagccg cagattccg             39

<210> SEQ ID NO 5
<211> LENGTH: 39
<212> TYPE: DNA
<213> ORGANISM: Artificial
<220> FEATURE:
<223> OTHER INFORMATION: primer

<400> SEQUENCE: 5
gccggtctcg ggaagcttct tgacctcggt agcgacaaa             39

<210> SEQ ID NO 6
<211> LENGTH: 43
<212> TYPE: DNA
<213> ORGANISM: Artificial
<220> FEATURE:
<223> OTHER INFORMATION: primer

<400> SEQUENCE: 6
cagtaagctt cccgagaccg gcgatatcca gatgactcag agc        43

<210> SEQ ID NO 7
<211> LENGTH: 36
<212> TYPE: DNA
<213> ORGANISM: Artificial
<220> FEATURE:
<223> OTHER INFORMATION: primer

<400> SEQUENCE: 7
actcgaaccc gccgtacgtt ttatctctac ctttgt                36

<210> SEQ ID NO 8
<211> LENGTH: 52
<212> TYPE: DNA
<213> ORGANISM: Artificial
<220> FEATURE:

<223> OTHER INFORMATION: primer

<400> SEQUENCE: 8
taatggccgg cctggccgcg gccgcttaaa gatcttcttc actaattaac tt   52

<210> SEQ ID NO 9
<211> LENGTH: 7
<212> TYPE: PRT
<213> ORGANISM: Artificial
<220> FEATURE:
<223> OTHER INFORMATION: Linker

<400> SEQUENCE: 9

Gly Gly Ser Ser Arg Ser Ser
1               5

<210> SEQ ID NO 10
<211> LENGTH: 7
<212> TYPE: PRT
<213> ORGANISM: Artificial
<220> FEATURE:
<223> OTHER INFORMATION: Linker

<400> SEQUENCE: 10

Gly Gly Ser Ser Arg Ser Ser
1               5

<210> SEQ ID NO 11
<211> LENGTH: 20
<212> TYPE: PRT
<213> ORGANISM: Artificial
<220> FEATURE:
<223> OTHER INFORMATION: Linker

<400> SEQUENCE: 11

Ser Ser Gly Gly Gly Gly Ser Gly Gly Gly Gly Gly Gly Ser Ser Arg
1               5                   10                  15

Ser Ser Gly Ser
            20

<210> SEQ ID NO 12
<211> LENGTH: 31
<212> TYPE: DNA
<213> ORGANISM: Artificial
<220> FEATURE:
<223> OTHER INFORMATION: primer

<400> SEQUENCE: 12
atgtcatatg gacattcaga tgacacagag t   31

<210> SEQ ID NO 13
<211> LENGTH: 46
<212> TYPE: DNA
<213> ORGANISM: Artificial
<220> FEATURE:
<223> OTHER INFORMATION: primer

<400> SEQUENCE: 13
ggaaccaccg ccggtctcgg gaagaagatc ttcttcacta attaac   46

<210> SEQ ID NO 14
<211> LENGTH: 74
<212> TYPE: DNA
<213> ORGANISM: Artificial
<220> FEATURE:
<223> OTHER INFORMATION: Primer

<400> SEQUENCE: 14
ggaagatcta gaggaaccac ccccaccacc gcccgagcca ccgccaccgg atgagccggt    60
ctcgggaaga agat    74

<210> SEQ ID NO 15
<211> LENGTH: 48
<212> TYPE: DNA
<213> ORGANISM: Artificial
<220> FEATURE:
<223> OTHER INFORMATION: primer

<400> SEQUENCE: 15
gagaccggcg gtggttcctc tagatcttcc caggctaagc cgcagatt    48

<210> SEQ ID NO 16
<211> LENGTH: 44
<212> TYPE: DNA
<213> ORGANISM: Artificial
<220> FEATURE:
<223> OTHER INFORMATION: primer

<400> SEQUENCE: 16
taatgcggcc gcttaatgat ggtgatggtg atgatgatga tggc    44

<210> SEQ ID NO 17
<211> LENGTH: 41
<212> TYPE: DNA
<213> ORGANISM: Artificial
<220> FEATURE:
<223> OTHER INFORMATION: primer

<400> SEQUENCE: 17
gtggttcctc tagatcttcc tcgaaggtcg cgggatatat t    41

<210> SEQ ID NO 18
<211> LENGTH: 49
<212> TYPE: DNA
<213> ORGANISM: Artificial
<220> FEATURE:
<223> OTHER INFORMATION: primer

<400> SEQUENCE: 18
taatggccgg cctggcctta atgatggtga tggtgatgat gatgatggc    49

<210> SEQ ID NO 19
<211> LENGTH: 42
<212> TYPE: DNA
<213> ORGANISM: Artificial
<220> FEATURE:
<223> OTHER INFORMATION: primer

<400> SEQUENCE: 19
ggttcctcta gatcttccgg aagccaggct aagccgcaga tt    42

<210> SEQ ID NO 20
<211> LENGTH: 4
<212> TYPE: PRT
<213> ORGANISM: Artificial
<220> FEATURE:
<223> OTHER INFORMATION: Amino Acid Sequence of Flag

<400> SEQUENCE: 20

Asp Tyr Lys Asp
1

<210> SEQ ID NO 21
<211> LENGTH: 120
<212> TYPE: PRT
<213> ORGANISM: Artificial
<220> FEATURE:
<223> OTHER INFORMATION: Amino Acid Sequence of VH

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 22
<211> LENGTH: 24
<212> TYPE: PRT
<213> ORGANISM: Artificial
<220> FEATURE:
<223> OTHER INFORMATION: Amino Acid Sequence of Linker

<400> SEQUENCE: 22

Ser Leu Glu Gly Thr Gly Gly Thr Ser Gly Ser Thr Ser Gly Thr Gly
1               5                   10                  15

Gly Ser Ser Arg Ser Ser Ser Thr
            20

<210> SEQ ID NO 23
<211> LENGTH: 10
<212> TYPE: PRT
<213> ORGANISM: Artificial
<220> FEATURE:
<223> OTHER INFORMATION: Amino Acid Sequence of Hemagglutinin (HA)

<400> SEQUENCE: 23

Tyr Pro Tyr Asp Val Pro Asp Tyr Ala Lys
1               5                   10

<210> SEQ ID NO 24
<211> LENGTH: 39
<212> TYPE: PRT
<213> ORGANISM: Artificial
<220> FEATURE:
<223> OTHER INFORMATION: Amino Acid Sequence of H1.winzipA1

<400> SEQUENCE: 24

Thr Val Ala Gln Leu Glu Glu Lys Val Lys Thr Leu Arg Ala Gln Asn
1               5                   10                  15

Tyr Glu Leu Lys Ser Arg Val Gln Arg Leu Arg Glu Gln Val Ala Gln
            20                  25                  30

Leu Ala Ser Glu Phe Glu Leu
        35

<210> SEQ ID NO 25
<211> LENGTH: 39
<212> TYPE: PRT
<213> ORGANISM: Artificial
<220> FEATURE:
<223> OTHER INFORMATION: Amino Acid Sequence of H2. winzipA2

<400> SEQUENCE: 25

Thr Val Ala Gln Leu Arg Glu Arg Val Lys Thr Leu Arg Ala Gln Asn
1               5                   10                  15

Tyr Glu Leu Glu Ser Glu Val Gln Arg Leu Arg Glu Gln Val Ala Gln
            20                  25                  30

Leu Ala Ser Glu Phe Glu Leu
        35

<210> SEQ ID NO 26
<211> LENGTH: 39
<212> TYPE: PRT
<213> ORGANISM: Artificial
<220> FEATURE:
<223> OTHER INFORMATION: Amino Acid Sequence of H3. Vel A1

<400> SEQUENCE: 26

Thr Val Ala Gln Leu Glu Glu Lys Val Lys Thr Leu Arg Ala Glu Asn
1               5                   10                  15

Tyr Glu Leu Lys Ser Glu Val Gln Arg Leu Glu Glu Gln Val Ala Gln
            20                  25                  30

Leu Ala Ser Glu Phe Glu Leu
        35

<210> SEQ ID NO 27
<211> LENGTH: 36
<212> TYPE: PRT
<213> ORGANISM: Artificial
<220> FEATURE:
<223> OTHER INFORMATION: Amino Acid Sequence of H4.Max

<400> SEQUENCE: 27

Thr Met Arg Arg Lys Asn Asp Thr His Gln Gln Asp Ile Asp Asp Leu
1               5                   10                  15

Lys Arg Gln Asn Ala Leu Leu Glu Gln Gln Val Arg Ala Leu Ala Ser
            20                  25                  30

Glu Phe Glu Leu
        35

<210> SEQ ID NO 28
<211> LENGTH: 52
<212> TYPE: PRT
<213> ORGANISM: Artificial
<220> FEATURE:
<223> OTHER INFORMATION: Amino Acid Sequence of H5. EE1234L

<400> SEQUENCE: 28

Thr Leu Glu Ile Glu Ala Ala Phe Leu Glu Gln Glu Asn Thr Ala Leu
1               5                   10                  15

Glu Thr Glu Val Ala Glu Leu Glu Gln Glu Val Gln Arg Leu Glu Asn
            20                  25                  30

Ile Val Ser Gln Tyr Glu Thr Arg Tyr Gly Pro Leu Gly Gly Ala Ser
            35                  40                  45

```
Glu Phe Glu Leu
    50

<210> SEQ ID NO 29
<211> LENGTH: 44
<212> TYPE: PRT
<213> ORGANISM: Artificial
<220> FEATURE:
<223> OTHER INFORMATION: Amino Acid Sequence of H6.VSAL E5

<400> SEQUENCE: 29

Thr Glu Val Ser Ala Leu Lys Glu Lys Val Ser Ala Leu Glu Lys Glu
1               5                   10                  15

Val Ser Ala Leu Lys Glu Lys Val Ser Ala Leu Glu Lys Glu Val Ser
            20                  25                  30

Ala Leu Glu Lys Gly Gly Ala Ser Glu Phe Glu Leu
        35                  40

<210> SEQ ID NO 30
<211> LENGTH: 31
<212> TYPE: PRT
<213> ORGANISM: Artificial
<220> FEATURE:
<223> OTHER INFORMATION: Amino Acid Sequence of H7.VSAL E3ox

<400> SEQUENCE: 30

Thr Cys Gly Gly Glu Val Ser Ala Leu Glu Lys Glu Val Ser Ala Leu
1               5                   10                  15

Glu Lys Glu Val Ser Ala Leu Glu Lys Ala Ser Glu Phe Glu Leu
            20                  25                  30

<210> SEQ ID NO 31
<211> LENGTH: 28
<212> TYPE: PRT
<213> ORGANISM: Artificial
<220> FEATURE:
<223> OTHER INFORMATION: Amino Acid Sequence of H8. IAALE3

<400> SEQUENCE: 31

Thr Glu Ile Ala Ala Leu Glu Lys Glu Ile Ala Ala Leu Glu Lys Glu
1               5                   10                  15

Ile Ala Ala Leu Glu Lys Ala Ser Glu Phe Glu Leu
            20                  25

<210> SEQ ID NO 32
<211> LENGTH: 107
<212> TYPE: PRT
<213> ORGANISM: Artificial
<220> FEATURE:
<223> OTHER INFORMATION: Amino Acid Sequence of VL

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 33
<211> LENGTH: 24
<212> TYPE: PRT
<213> ORGANISM: Artificial
<220> FEATURE:
<223> OTHER INFORMATION: Amino Acid Sequence of Linker

<400> SEQUENCE: 33

Ala Leu Glu Gly Thr Gly Ser Ser Thr Gly Ser Ser Thr Gly Pro Gly
1               5                   10                  15

Gly Ser Ser Arg Ser Ser Ser Thr
            20

<210> SEQ ID NO 34
<211> LENGTH: 15
<212> TYPE: PRT
<213> ORGANISM: Artificial
<220> FEATURE:
<223> OTHER INFORMATION: Amino Acid Sequence of myc

<400> SEQUENCE: 34

Glu Gln Lys Leu Ile Ser Glu Glu Asp Leu Lys Leu Pro Glu Thr
1               5                   10                  15

<210> SEQ ID NO 35
<211> LENGTH: 39
<212> TYPE: PRT
<213> ORGANISM: Artificial
<220> FEATURE:
<223> OTHER INFORMATION: Amino Acid Sequence of L1.wizipB1

<400> SEQUENCE: 35

Ser Val Asp Glu Leu Gln Ala Glu Val Asp Gln Leu Gln Asp Glu Asn
1               5                   10                  15

Tyr Ala Leu Lys Thr Lys Val Ala Gln Leu Arg Lys Lys Val Glu Lys
            20                  25                  30

Leu Ala Ser Glu Phe Glu Leu
        35

<210> SEQ ID NO 36
<211> LENGTH: 50
<212> TYPE: PRT
<213> ORGANISM: Artificial
<220> FEATURE:
<223> OTHER INFORMATION: Amino Acid Sequence of L2.winzipB2

<400> SEQUENCE: 36

Gly Pro Gly Gly Ser Ser Arg Ser Ser Ser Thr Ser Val Asp Glu Leu
1               5                   10                  15

Lys Ala Glu Val Asp Gln Leu Gln Asp Gln Asn Tyr Ala Leu Arg Thr
            20                  25                  30

Lys Val Ala Gln Leu Arg Lys Val Glu Lys Leu Ser Glu Glu Phe
        35                  40                  45

Glu Leu
    50

<210> SEQ ID NO 37
```

<211> LENGTH: 50
<212> TYPE: PRT
<213> ORGANISM: Artificial
<220> FEATURE:
<223> OTHER INFORMATION: Amino Acid Sequence of L3. Vel B1

<400> SEQUENCE: 37

Gly Pro Gly Gly Ser Ser Arg Ser Ser Thr Ser Val Asp Glu Leu
1               5                   10                  15

Gln Ala Glu Val Asp Gln Leu Glu Asp Glu Asn Tyr Ala Leu Lys Thr
                20                  25                  30

Lys Val Ala Gln Leu Arg Lys Lys Val Glu Lys Leu Ala Ser Glu Phe
        35                  40                  45

Glu Leu
    50

<210> SEQ ID NO 38
<211> LENGTH: 47
<212> TYPE: PRT
<213> ORGANISM: Artificial
<220> FEATURE:
<223> OTHER INFORMATION: Amino Acid Sequence of L4. myc

<400> SEQUENCE: 38

Gly Pro Gly Gly Ser Ser Arg Ser Ser Thr Ser Val Gln Ala Glu
1               5                   10                  15

Glu Gln Lys Leu Ile Ser Glu Glu Asp Leu Leu Arg Lys Arg Arg Glu
                20                  25                  30

Gln Leu Lys His Lys Leu Glu Gln Leu Ala Ser Glu Phe Glu Leu
        35                  40                  45

<210> SEQ ID NO 39
<211> LENGTH: 64
<212> TYPE: PRT
<213> ORGANISM: Artificial
<220> FEATURE:
<223> OTHER INFORMATION: Amino Acid Sequence of L5. RR1234L

<400> SEQUENCE: 39

Gly Pro Gly Gly Ser Ser Arg Ser Ser Thr Ser Lys Gly Gly Gly
1               5                   10                  15

Leu Glu Ile Arg Ala Ala Phe Leu Arg Arg Arg Asn Thr Ala Leu Arg
                20                  25                  30

Thr Arg Val Ala Glu Leu Arg Gln Arg Val Gln Arg Leu Arg Asn Ile
        35                  40                  45

Val Ser Gln Tyr Glu Thr Arg Tyr Gly Pro Ala Ser Phe Glu Glu Leu
    50                  55                  60

<210> SEQ ID NO 40
<211> LENGTH: 52
<212> TYPE: PRT
<213> ORGANISM: Artificial
<220> FEATURE:
<223> OTHER INFORMATION: Amino Acid Sequence of L6. VSAL K5

<400> SEQUENCE: 40

Gly Pro Gly Gly Ser Ser Arg Ser Ser Thr Lys Val Ser Ala Leu
1               5                   10                  15

Lys Glu Lys Val Ser Ala Leu Lys Glu Lys Val Ser Ala Leu Lys Glu
                20                  25                  30

Lys Val Ser Ala Leu Lys Glu Lys Val Ser Ala Leu Lys Glu Gly Gly
        35                  40                  45

Glu Phe Glu Leu
    50

<210> SEQ ID NO 41
<211> LENGTH: 41
<212> TYPE: PRT
<213> ORGANISM: Artificial
<220> FEATURE:
<223> OTHER INFORMATION: Amino Acid Sequence of L7. VSAL k3ox

<400> SEQUENCE: 41

Gly Pro Gly Gly Ser Ser Arg Ser Ser Thr Cys Gly Gly Lys Val
1               5                   10                  15

Ser Ala Leu Lys Glu Lys Val Ser Ala Leu Lys Glu Lys Val Ser Ala
            20                  25                  30

Leu Lys Glu Gly Gly Glu Phe Glu Leu
        35                  40

<210> SEQ ID NO 42
<211> LENGTH: 39
<212> TYPE: PRT
<213> ORGANISM: Artificial
<220> FEATURE:
<223> OTHER INFORMATION: Amino Acid Sequence of L8.IAAL K3

<400> SEQUENCE: 42

Gly Pro Gly Gly Ser Ser Arg Ser Ser Thr Ser Lys Ile Ala Ala
1               5                   10                  15

Leu Lys Glu Lys Ile Ala Ala Leu Lys Glu Lys Ile Ala Ala Leu Lys
            20                  25                  30

Glu Ala Ser Glu Phe Glu Leu
        35

<210> SEQ ID NO 43
<211> LENGTH: 129
<212> TYPE: PRT
<213> ORGANISM: Artificial
<220> FEATURE:
<223> OTHER INFORMATION: Amino Acid Sequence of C1. H-G44C

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Cys Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Tyr Pro Tyr Asp Val Pro Asp Tyr
        115                 120                 125

Ala

-continued

```
<210> SEQ ID NO 44
<211> LENGTH: 129
<212> TYPE: PRT
<213> ORGANISM: Artificial
<220> FEATURE:
<223> OTHER INFORMATION: Amino Acid Sequence of C2. H-Q105C

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Cys
            100                 105                 110

Gly Thr Leu Val Thr Val Ser Ser Tyr Pro Tyr Asp Val Pro Asp Tyr
        115                 120                 125

Ala

<210> SEQ ID NO 45
<211> LENGTH: 117
<212> TYPE: PRT
<213> ORGANISM: Artificial
<220> FEATURE:
<223> OTHER INFORMATION: Amino Acid Sequence of C3. L-A43C

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Cys Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Glu Gln Lys Leu Ile
            100                 105                 110

Ser Glu Glu Asp Leu
        115

<210> SEQ ID NO 46
<211> LENGTH: 117
<212> TYPE: PRT
<213> ORGANISM: Artificial
<220> FEATURE:
<223> OTHER INFORMATION: Amino Acid Sequence of C4. L-Q100C

<400> SEQUENCE: 46
```

-continued

```
Asp Ile Gln Met Thr Gln Ser Pro Ser Ser Leu Ser Ala Ser Val Gly
 1           5               10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35              40              45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65              70                  75                      80

Glu Asp Phe Ala Thr Tyr Tyr Cys Gln Gln His Tyr Thr Thr Pro Pro
                 85                  90                  95

Thr Phe Gly Cys Gly Thr Lys Val Glu Ile Lys Glu Gln Lys Leu Ile
            100                 105                 110

Ser Glu Glu Asp Leu
            115
```

PROTEIN COMBINATION-BASED FV LIBRARY, AND PREPARATION METHOD THEREFOR

CROSS-REFERENCE TO RELATED APPLICATIONS

This application is a U.S. national phase under the provisions of 35 U.S.C. § 371 of International Patent Application No. PCT/KR14/00697 filed Jan. 24, 2014, which in turn claims priority of U.S. Provisional Patent Application No. 61/756,066 filed Jan. 24, 2013. The disclosures of such international patent application and U.S. Provisional priority patent application are hereby incorporated herein by reference in their respective entireties, for all purposes.

TECHNICAL FIELD

The present invention relates to a method for constructing an Fv library based on a combination of proteins, a method of screening a desired antibody using the constructed Fv library, an Fv antibody screened by the screening method, and an Fv library constructed by the Fv library construction method.

BACKGROUND ART

Antibodies are proteins produced by the B-lymphocytes of the immune system in response to antigens, recognize antigens and bind to antigens. Such antibodies are regarded as new protein drug candidates for treating diseases. To find desired functional antibodies, various antibody libraries are constructed, and the functional antibodies are screened from antibody libraries. Such antibody libraries are constructed using gene recombination technology. Specifically, genes encoding antibody proteins are extracted from B-cells in the human body to construct antibody gene libraries, and antibodies having desired antigen binding specificity are screened from the libraries. Antibody library technology brought about a revolution in the construction of antibodies such as human antibodies. The most prominent characteristic of antibody immune responses is that antibody binding specifically to a kind or shape of antigen could be made within one week, if the antigen is a foreign substance different from an in vivo component. Antibodies are produced by B-lymphocytes, and a single B lymphocyte produces only one type of antibody. In fact, it is known that numerous B lymphocytes exist in the human body, and each B lymphocyte expresses an antibody having unique antigen binding specificity on the cell membrane. It is generally known that an antigen binding diversity of about $10^8$ exists in the human body. When an antigen invades the body, only B lymphocytes expressing an antibody that binds specifically to the antigen proliferate rapidly while producing a large amount of the antibody, and as a result, the concentration of the antibody in the serum increases rapidly to thereby quickly eliminate the invaded antigen. Thus, an antibody diversity of several hundred millions exists in the human body, and this antibody diversity is referred to as repertoire. Thus, when a sufficient number of B lymphocytes are collected from the human body by blood collection, after which mRNA is isolated from the cells and synthesized into cDNA encoding the heavy-chain and light-chain variable regions of antibody by RT-PCR (reverse transcriptase-polymerase chain reaction), a human antibody repertoire can be constructed in vitro in the form of genes in a relatively simple manner. The key of antibody library technology is to express (or display) this human antibody gene repertoire as protein while paring a gene encoding the antibody protein through any medium (genotype-phenotype linkage), thereby testing an antibody binding to a specific antigen screened from the antibody library and obtaining a gene encoding the specific antibody. Herein, perfect immunity is not required, the repertoire is either displayed as Fab of an antibody having antigen binding function, or displayed as an antibody fragment, named scFv (single-chain variable fragment) in which the heavy-chain and light-chain variable domains ($V_H$ and $V_L$) are connected to each other by a short peptide linker of about 15 amino acids. Herein, the display is classified into phage display, ribosome display, yeast display and the like according to the kind of medium that is used in the genotype-phenotype linkage, and an antibody having desired antigen binding characteristics can be obtained without inducing an immune response by administration of an antigen. However, there are shortcomings in that a lot of know-how is required for antibody library construction and antibody screening, it is not easy to obtain high-affinity antibodies, and thus antibody optimization procedures such as affinity maturation are frequently performed after antibody screening, and functional analysis in mammalian cells cannot be performed due to problems such as toxicity, particularly during first-step screening. Such shortcomings have become a barrier for the development of therapeutic antibodies, because therapeutic antibodies do not simply bind to antigens but should have therapeutic functions.

Among antibody libraries, phage display antibody libraries are currently most frequently used. In fact, Humira (anti-TNF-alpha human monoclonal antibody) which is a currently commercially available rheumatoid arthritis therapeutic agent is a therapeutic antibody made by phage display technology. An ideal antibody library contains enormous antibody diversity, and thus high-affinity antibody clones having desired antigen binding specificity can be screened therefrom. For this purpose, a library having an antibody library of about $10^{10}$-$10^{11}$ should be constructed. However, it is very difficult to construct a library having this size by antibody gene cloning, and this is considered as the most difficult problem in the construction of phage display antibody libraries. In addition, there is a shortcoming in that functional analysis cannot be directly performed, because phages themselves act to be toxic. The biggest advantage of ribosome display technology is a cell-free system, and thus theoretically, libraries having a large size of $10^{13}$ can be easily constructed by ribosome display technology. Thus, ribosome display technology is advantageous for the screening of high-affinity antibodies (generally, the size of an antibody library becomes larger, the possibility for high-affinity antibodies to be contained in the library is higher). In addition, because PCR amplification is performed in ribosome display technology, error-prone polymerase or the like can be used, and thus the introduction of mutation for artificially inducing is very easy. However, ribosome display technology also has toxicity problems and various experimental problems. For this reason, phage display technology is mainly used for the construction of antibody libraries of naive origin. In yeast display technology, there are many technical limitations in making antibody libraries having a diversity of $10^9$ or more, because a process of inserting a recombinant vector into a S. cerevisiae strain is required and the size of yeast cells is large. Thus, yeast display technology is mainly used to construct a mutant library of already established antigen-specific antibodies and to screen high-affinity antibodies from the mutant library.

However, in such antibody libraries, all antibodies are not individually separated, but are mixed together. Such antibody libraries have limitations in that screening of an antibody to a target antigen based on its function (activity) is not actually impossible, and only screening of an antibody based on binding to an antibody is possible. Initial antibody candidates obtained in this procedure are examined for their function in a subsequent step to select antibodies having functions. In most cases, antibodies, which easily bind but have no function, are obtained in the selection step. Thus, a new method that overcomes the limitation of this screening method is required. In other words, a method of screening antibodies based on their function from beginning is required. However, existing libraries are in a state in which various antibodies are mixed together, and it is impossible to screen individual antibodies based on its function. Thus, if it is possible to individually purify and store all antibodies in specially addressed library, like low-molecular-weight compound libraries, it is possible to screen antibodies based on their function. However, because antibodies are proteins, processes for expressing and purifying antibodies are required, and thus it is actually impossible to construct a library of 100,000 or 1,000,000 different antibodies. In other words, conventional methods have shortcomings in that, when the library diversity is assumed to be 1,000,000, the purification of 1,000,000 proteins is required, and the number of required protein purifications increases by exponentially as the diversity increases. Conventional library construction technologies include a technology of constructing a library by combining $V_H$ and $V_L$ at the DNA level in a vector (U.S. Pat. No. 8,178,320), a technology of constructing a library of antibody light chains and heavy chains at the DNA level (U.S. Pat. No. 7,858,559), etc. However, these library construction technologies have shortcomings in that the purification of a desired number of proteins is required to construct a library having a diversity satisfying a combination of the proteins at the DNA level, and the functions of the antibodies in the constructed library cannot be immediately analyzed due to the geometric number of the antibodies, and for this reason, an additional step of reducing the number of antibodies, which can be screened by binding to antigens and analyzed for their function, is required, and a true important antibody can be missed during this screening. Particularly, in conventional library construction methods, Fvs should be expressed in combination at the DNA level, and thus the purification of proteins corresponding to the library diversity is required. Thus, in the conventional library construction methods, it is impossible to construct a library containing individually separated antibodies.

Under such circumstances, the present inventors have made extensive efforts to develop a library in which antibodies are individually separated so that they can be functionally screened. As a result, the present inventors have paid attention to the construction of library, in which combinations happened at the protein level, unlike conventional library construction technologies of combining antibody domains at the DNA level, and have found that an Fv library based on a combination of proteins can be constructed by combining $V_H$ and $V_L$ at the protein level, thereby completing the present invention.

DISCLOSURE OF INVENTION

Technical Problem

It is an object of the present invention to provide a method for constructing an Fv (variable fragment) library based on a combination of proteins.

Another object of the present invention is to provide a method of screening a desired antibody using an Fv library constructed by the above method for constructing an Fv library based on a combination of proteins.

Still another object of the present invention is to provide a desired Fv antibody screened by the above screening method.

Yet another object of the present invention is to provide an Fv library constructed by the above method for constructing an Fv library based on a combination of proteins.

Technical Solution

To achieve the above objects, in one aspect, the present invention provides an Fv (variable fragment) library based on a combination of proteins and a method for constructing the same. Specifically, the present invention provides an Fv library based on a combination of proteins, the Fv library comprising $V_H$ domain proteins linked with $V_L$ domain proteins.

The present invention also provides a method for constructing an Fv library based on a combination of proteins, the method comprising the steps of: (a) preparing heavy-chain variable region ($V_H$) domain proteins and light-chain variable region ($V_L$) domain proteins; and (b) paring the $V_H$ domain proteins and the $V_L$ domain proteins, prepared in step (a), to one another.

BRIEF DESCRIPTION OF THE DRAWINGS

FIG. 6 shows a comparison of the expressions and purification yields of recombinant proteins between the presence and absence of sortase and the presence and absence of Flag.

FIG. 19 shows the results of analyzing high frequency for introducing the $V_H$ CDR and $V_L$ CDR diversity.

FIG. 20 shows the results of designing a library having diversity according to an example of the present invention.

FIG. 23 shows a library screening process.

BEST MODE FOR CARRYING OUT THE INVENTION

Figure 1:
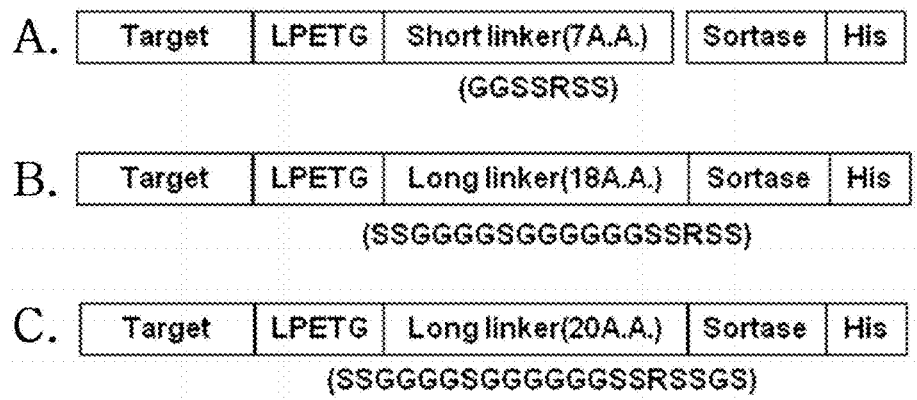
FIG. 1 schematically shows fusion proteins, each comprising target-LPETG-linker (having any one of various lengths)-Sortase-His tag. (A): a linker consisting of 7 amino acids, (B): a linker consisting of 18 amino acids, and (C): a linker consisting of 20 amino acids.

As used herein, the term "Fv (variable fragment) library" refers to a collection of a number of Fvs having diversity. As used herein, the term "Fv (variable fragment)" refers to the minimum antibody fragment that is a portion of the Fab (fragment antigen binding) region of the antibody, which consists of a heavy-chain variable region ($V_H$) and a light-chain variable region ($V_L$). For the purpose of the present invention, the Fv (variable fragment) library may be an Fv library based on a combination of proteins.

Conventional libraries were constructed by combining antibodies at the DNA level in order to meet antibody gene repertoires which are a diversity of antibodies. Generally, antibodies are produced by B-lymphocytes, and a single B lymphocyte produces only one type of antibody. It is known that numerous B lymphocytes exist in the human body, and each B lymphocyte expresses an antibody having unique antigen binding specificity on the cell membrane. Also, it is generally known that an antigen binding diversity of about $10^8$ exists in the human body. Thus, an antibody diversity of several hundred millions exists in the human body. To form a repertoire that is such antibody diversity, a combination of several hundred million DNAs should be constructed, and antibodies should be prepared therefrom. For example, when a library having a diversity of $10^8$ is to be constructed, 100,000,000 DNAs should be synthesized, and 100,000,000 protein purifications should be performed to construct a library of isolated protein antibodies, but this is actually almost impossible. However, according to the present invention, an Fv library comprising specially addressed antibodies can be constructed by the expression and purification of 10,000 $V_H$ domains and 10,000 $V_L$ domains, that is, the expression and purification of only 20,000 domains. This method for constructing an Fv library based on a combination of proteins according to the present invention was first developed by the present inventors. The method for constructing an Fv library based on a combination of proteins according to the present invention is characterized in that an Fv library based on a desired combination of proteins can be constructed by pairing purified $V_H$ domains and $V_L$ domains outside cells, not inside cells.

Preferably, the Fv library enables functional analysis of individual members thereof.

Preferably, the functional analysis of individual members may, or more preferably may not comprise a pre-screening step based on binding to a target.

As described above, conventional libraries are DNA-based libraries. In this case, the expression and isolation of antibody proteins from DNAs require many expression and purification processes, and thus the antibodies are not individually separated in the library, but are mixed together in the library. For this reason, a step of isolating and purifying protein antibodies is required in order to examine the function of the protein antibodies. However, as described above, this step is practically impossible. For this reason, antibodies are first screened based on their binding to a target substance such as antigen, and then only antibodies bound to the target substance are examined for their function in a second screening step. However, when antibodies are screened based on their binding to a target substance as described above, an antibody having a desired function can be missed. However, members of the Fv library of the present invention can be individually separated, and thus can be individually analyzed without a pre-screening step based on binding to a target. According to the Fv library of the present invention, Fv antibodies having practical function can be screened without missing.

For the purpose of the present invention, the Fv library may be an Fv library including $V_H$ domains and $V_L$ domains and constructed by the combination of heavy-chain variable region ($V_H$) domain proteins and light-chain variable region ($V_L$) domain proteins, but may include antigen binding forms of antibodies, including CH-containing fragments having antigen binding capability (e.g., Fab', F(ab')2, Fab, Fv and rIgG), as well as full-length antibodies. Also, the antibodies may include recombinant single chain Fv fragments (scFv), bivalent or bispecific molecules, diabodies, triabodies, and tetrabodies. The bivalent and bispecific molecules, for example, are described in Kostelny et al. (1992, J. Immunol., 148:1547), Pack and Pluckthun (1992, Biochemistry, 31:1579), Hollinger et al. (1993, Supra), Gruber et al. (1994, J. Immunol., 5368), Zhu et al. (1997, Protein Sci., 6:781 et al.), Hu et al. (1996, Cancer Res., 56:3055), Adams et al. (1993, Cancer Res., 53:4026), and McCartney et al. (1995, Protein Eng., 8:301).

The full-length antibodies include IgA, IgD, IgE, IgM and IgG, and IgG is subdivided into IgG1, IgG2, IgG3 and IgG4 subtypes. Fab has light-chain and heavy-chain variable regions, a light-chain constant region, and a first heavy-chain constant region (CH1), and includes one antigen-binding site. Fab' differs from Fab in that it has a hinge region including at least cysteine residue in the C-terminal region of the heavy-chain CH1 domain. F(ab')$_2$ antibody is produced when cysteine residues in the hinge region of Fab' form a disulfide bond.

Step (a) of preparing heavy-chain variable region ($V_H$) domain proteins and light-chain variable region ($V_L$) domain proteins may preferably be performed by introducing desired diversity into the $V_H$ domain protein and the $V_L$ domain protein. The introduction of diversity may be performed by any known mutation method. In addition, the $V_H$ domain proteins and the $V_L$ domain proteins can be prepared by any known method. For the construction of the Fv library including the $V_H$ domain proteins and the $V_L$ domain proteins, protein sequences can be selected using database including all tertiary structures of human proteins, such as PDB (Protein Data Bank) and SCOP (Structural Classification of Protein). In addition, protein sequences for the construction of the library can be selected through various databases including known human or non-human protein sequences, but the scope of the present invention is not limited thereto. In addition, $V_H$ and $V_L$ sequences can be selected from known variable region sequences such as those available the Kabat antibody database (www.bioinf.org.uk/abs/simkab.html) and NCBI database (www.ncbi.nlm.nkh.gov), and from protein databases such as UniProt (www.ebi.uniprot.org) and PRF/SEQDB (www.prf.or.jp) to design the library of $V_H$ and $V_L$ sequences. In addition, these can be supplemented by collection of human VH and VL sequences by direct sequencing of amplified VH and VL mRNA from one or more individual donors. Various combinations of domains can be considered for design of $V_H$ and $V_L$ domain proteins. In the selection of sequences, only antibody domain sequences excluding T cell receptors or other Ig sequences can be selected by a known method. In an example of the present invention, antibody domain sequences were selected using the HMMER program in the PISEC sever (Example 6).

The $V_H$ domain proteins and the $V_L$ domain proteins may be of human or non-human origin.

Preferably, a mutation can be introduced into the CDR (complementarity-determining region) in the $V_H$ domain protein or $V_L$ domain protein. The CDR may be one or more selected from among CDR1, CDR2 and CDR3. Preferably, the CDR may be one, two or three selected from among CDR1, CDR2 and CDR3, but is not limited thereto. More preferably, it may be CDR3, but a mutation can be introduced into the CDR without limitation depending on the kind of desired antibody. In an example of the present invention, diversity was changed by introducing a mutation into CDR3 while fixing CDR1 and CDR2 (Example 8).

Preferably, a mutation may be introduced into the framework in the $V_H$ domain protein or $V_L$ domain protein.

Preferably, the protein-protein paring in step (b) of randomly paring the $V_H$ domain proteins and $V_L$ domain proteins, prepared in step (a), to each other, may be selected from the group consisting of: (i) paring between wild-type domains; (ii) paring by disulfide bonds between cysteines introduced in the domain proteins; (iii) paring by fusion between coiled-coil domains; (iv) paring by protein-protein interaction; and (v) combinations thereof. Herein, (i) to (iv) include any known paring method without limitation. For example, the protein-protein paring may be performed by each of (i) to (iv) or a combination of two or more of (i) to (iv).

Preferably, (i) paring between wild-type domains may be performed by known pairing between wild-type $V_H$ domain proteins and $V_L$ domain proteins. In an example of the present invention, wild-type paring (pairing) was confirmed (Experimental Example 2).

Preferably, in (ii) paring by disulfide bonds between cysteines, cysteine may be introduced into each of the $V_H$ domain proteins and the $V_L$ domain proteins by a known method so that the $V_H$ domain proteins and the $V_L$ domain proteins can be paired by disulfide bonds between the cysteines introduced therein. In an example of the present invention, disulfide bonding (pairing) was confirmed (Experimental Examples 1 to 4).

Preferably, in (iii) paring by fusion between coiled-coil domains, a coiled-coil domain may be introduced into each of the $V_H$ domain proteins and the $V_L$ domain proteins so that the $V_H$ domain proteins and the $V_L$ domain proteins can be paired therebetween by the coiled-coil bond. This coiled-coil domain can be obtained from known databases or the like, and can be prepared using the method disclosed by Katja M. Arndt et al. (J. Mol. Biol. (2001) 312, 221-228). In addition, sequences disclosed by Jennifer R. et al. (J. Biol. Chem. (2002) 277, 37272-37279), J. R. Litowski (J. peptide Res. (2001) 58, 477-492), Jesus Fernandez-Rodriguez et al. (protein science (2012) 21, 511-591), Katja M. Arndt et al. (Structure (2002) 10, 1235-1248), Katja M. Arndt et al. (J. Biol. Chem. (2000) 295, 627-639), etc. may preferably be used, but all coiled-coil domains having regularity may be used in the present invention. The coiled-coil domain that is used in the present invention is not limited to the sequences disclosed in the above papers. In an example of the present invention, pairing with coiled-coil binding was confirmed (Experimental Examples 1 to 4).

Preferably, (iv) paring by protein-protein interaction includes paring by known protein-protein interaction. For example, protein-protein paring such as leucine-zipper, like JUN domain and FOS domain, may be used. In addition, various known interactions, including non-covalent interaction, engineered CH domain and engineered interaction surface, may be used.

In one embodiment, paring in step (b) may be achieved by random pairing or target pairing.

Preferably, the method for constructing the Fv library based on the combination of proteins may further comprise step (c) of identifying (ID) numbers given to individual compartments, in which desired assembled Fvs are stored.

The assembled Fvs can be obtained by random pairing or target pairing. In the case of the target paring, the method may comprise constructing the library in such a manner that the $V_H$ domains and the $V_L$ domains whose information is known do not overlap. Preferably, in the case of the target pairing, the method may comprise performing the pairing of known $V_H$ and $V_L$ to obtain assembled Fvs, recovering the assembled Fvs, storing the recovered Fvs in individual compartments given ID numbers, and confirming the information of the $V_H$ and $V_L$ domains in the individual compartments given ID numbers.

Because members of the Fv library of present invention can be individually separated, the present invention could provide library with members that may be stored in individual compartments. The individual compartments given ID numbers may be provided in various devices, including plates, test tubes, arrays and the like, but are not limited thereto. In addition, the compartments may further include buffer, a protein stabilizer or the like.

In another aspect, the present invention provides a method for screening a desired Fv antibody, the method comprising the steps of: (a) constructing an Fv library based on a combination of proteins according to the above Fv library construction method; and (b) performing individual functional analysis for a desired property, characteristic or activity using the Fv library.

The method for constructing the Fv library is as described above.

Preferably, the desired property, characteristic or activity may be cell proliferation, differentiation or cell death.

The desired property, characteristic or activity may be protein-protein aggregation, an increase in protein stability, increased protein solubility, introduction of a glycosylation site, introduction of a conjugated site, a decrease in immunogenicity, an increase in protein expression, an increase in antigen affinity, a decrease in antigen affinity, a change in binding affinity, a change in immunogenicity, or enforcement of specificity, but is not limited thereto.

Preferably, the screening method may further comprise (c) step of identifying the identification (ID) number of a compartment having the desired Fv antibody stored therein.

Preferably, the screening method may comprise steps of: (c) identifying the ID number of a compartment having the desired Fv antibody stored therein; and (d) identifying the $V_H$ domain protein and $V_L$ domain protein of the Fv antibody of the identified compartment.

If the $V_H$ domain protein and $V_L$ domain protein of the Fv antibody of the identified compartment are identified, only the desired Fv antibody comprising a combination of the $V_H$ domain protein and the $V_L$ domain protein can be amplified.

Preferably, the screening method may further comprise steps of: (c) identifying the ID number of a compartment having the desired Fv antibody stored therein; and (d) identifying the DNA sequence of the Fv antibody.

If the Fv antibody is identified from the identified compartment and the DNA or amino acid sequence thereof is analyzed readily, only the desired Fv antibody can be amplified.

In another aspect, the present invention provides a desired Fv antibody screened by the screening method.

In another aspect, the present invention provides an Fv library based on a combination of proteins, constructed by the method for constructing an Fv library based on a combination of proteins.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1: Preparation of Expression Vector

1-1: Preparation of BAP-sortase-LPETG-target ($V_L$)

The PCR conditions used in Example 1 of the present invention are as following.

A PCR mixture consisted of 31.5 µl of distilled water, 10 µl of 5× PrimeSTAR buffer, 5 µl of dNTP (2.5 mM), 1 µl of forward primer (100 µM), 1 µl of reverse primer (100 µM), 1 µl of template (100 ng/µl), and 0.5 µl of PrimeSTAR polymerase (2.5 u/µl). PCR was performed for 30 cycles, each consisting of 98° C. for 10 sec and 68° C. for 1 min, and the PCR product was stored at 4° C.

As a template, BAP, sortase, target sequence were synthesized and used.

Specifically, the primers used are as follows.

First, a DNA sequence encoding BAP (biotin acceptor peptide) was amplified by PCR using primer 1_sfi (5'-ccgt ggcccaggcggcc GCA AGC AGC GGC CTG AAC GAC ATC TTC GAG GCC-3': SEQ ID NO: 1) or primer (5'-ATGT CATATG GCA AGC AGC GGC CTG AAC GAC ATC TTC GAG GCC-3': SEQ ID NO: 2) and primer 2 (5'-CTG-CATTTCGTGCCACTCGATCTTCTGGGCCTCGAAGA TGTCGTT-3': SEQ ID NO: 3).

A DNA sequence encoding an amino acid sequence comprising amino acids 60 to 206 of SrtA (GenBank Accession No. AF162687) was amplified by PCR using primer 3 (5'-ATC GAG TGG CAC GAA ATG CAG GCT AAG CCG CAG ATT CCG-3': SEQ ID NO: 4) and primer 4 (5'-GCCGGTCTCGGGAAGCTTCTTGACCTCGGTAGCG ACAAA-3': SEQ ID NO: 5).

A second DNA sequence encoding LPETG-target ($V_L$) was amplified by PCR using primer 5 (5'-CAG TAA GCT TCC CGA GAC CGG CGAT ATC CAG ATG ACT CAG AGC-3': SEQ ID NO: 6), primer 6 (5'-ACTCGAACCCGC-CGTACGTTTTATCTCTACCTTTGT-3': SEQ ID NO: 7) and template target ($V_L$).

Next, the three PCR products were mixed with one another, and then a DNA sequence encoding the fusion protein BAP-SrtA-kLPETG-target ($V_L$) having a HindIII site between SrtAc-LPETG and a target-encoding sequence was amplified by PCR using primer 1_sfi or primer 1 and primer 7 (5'-taat ggccggcctggcc GC GGC CGC TTAAA GATCTTCTTCACTAATTAACTT-3': SEQ ID NO: 8).

The resulting DNA fragment was digested with NdeI and NotI, ligated to a pET23a vector (Novagen), digested with SfiI, and then ligated into the vector pCom3× that expresses the fusion protein BAP-sortase-LPETG-target.

1-2: Preparation of Target ($V_L$)-kLPETG-Other Linker-Sortase-H10

A DNA sequence encoding target-LPETG-linker (7 a.a.), with which linker (7a.a.) (GGSSRSS: SEQ ID NO: 9) was bonded, was amplified by PCR using primers 8 (5'-ATGT CATATG GAC ATT CAG ATG ACA CAG AGT-3': SEQ ID NO: 12) and primer 9 (5'-ggaaccaccgccggtctcgg gaag AAGATCTTCTTCACTAATTAAC-3': SEQ ID NO: 13).

Using primer 8, primer 10 (5'-GGA AGA TCT AGA GGA ACC ACC CCC ACC ACC GCC CGA GCC ACC GCC ACC GGA TGA GCC GGT CTC GGG AAG AAG AT-3': SEQ ID NO: 14) and the PCR product target-LPETG-linker (7 a.a.), a DNA sequence encoding target-LPETG-linker (18 a.a.) linked with a linker (18 a.a.) (SSGGGG SGGGGGGSSRSS: SEQ ID NO: 10) was amplified by PCR.

A DNA sequence encoding linker (7 a.a.)-SrtA (60-206) was amplified by PCR using primer 11 (5'-gag acc ggc ggt ggt tcc tct aga tct tcc cag gct aag ccg cag att-3': SEQ ID NO: 15) and primer 12. (5'-taat GC GGC CGC tta atgatggtgATG-GTGATGATGATGATGGC-3': SEQ ID NO: 16)

A DNA sequence encoding linker (18 a.a.)-SrtA (60-206) was amplified by PCR using primer 13 (5'-gtggttcctctagatcttcc tcg aag gtc gcg gga tat att-3': SEQ ID NO: 17) and primer 14 (5'-taat ggccggcctggcc tta atgatggtgatggtgatgatgatgatggc-3': SEQ ID NO: 18).

A DNA sequence encoding linker (20 a.a.)-SrtA (60-206) linked with (20 a.a.) linked with a linker (20 a.a.) (SSGGGGSGGGGGGSSRSSGS: SEQ ID NO: 11) was amplified by PCR using primer 15 (5'-ggt tcc tct aga tct tcc gga agc cag gct aag ccg cag att-3': SEQ ID NO: 19) and primer 14.

Finally, target (VL)-LPETG-Linker (7a.a.)-Sortase-H10 (FIG. 1A) was amplified by overlapping PCR using primer 8, primer 12 and a mixture of the PCR products (target-LPETG-linker (7 a.a.) and linker (7 a.a.)-SrtA).

A gene encoding target (VL)-LPETG-linker (18 a.a.)-Sortase-H10 (FIG. 1B) was amplified by overlapping PCR using primer 8, primer 14 and a mixture of the PCR products (target-LPETG-linker (18 a.a.) and linker (18 a.a.)-SrtA).

A gene encoding target (VL)-LPETG-linker (20 a.a.)-Sortase-H10 (FIG. 1C) was amplified by overlapping PCR using primer 8, primer 14 and a mixture of the PCR products (target-LPETG-linker (18 a.a.) and linker (20 a.a.)-SrtA).

Each of the resulting DNA fragments was digested with NdeI and NotI, and ligated to the vector pET23a (Novagen) that expresses the fusion protein target-LPETG-other linker-Sortase-H10.

The fusion protein target-kLPETG-linker (20 a.a.)-Sortase-H10 has a HindIII site between the target and the sequence encoding kLPETG-linker (20 a.a.)-Sortase-H10. Next, for expression, all the gene constructs were digested with NdeI and HindIII and ligated to pET23a-kLPETG-linker(20a.a.)-Sortase-H10.

Example 2: Analysis of Expression

All expression experiments were performed using *E. coli* Origami2(DE3). A single bacterial colony was inoculated into a dYT medium (30 ml) containing 100 mg/l of ampicillin and 0.5% (w/v) glucose and was cultured overnight at 37° C. The preculture was inoculated into 0.3 l of dYT medium (100 mg/l of ampicillin and 50 mM $K_2HPO_4$) and cultured at 37° C. (1 μl flask with baffles, 200 rpm). When the $OD_{600}$ value reached 0.6, IPTG was added to a final concentration of 0.5 mM to induce expression. The culture was maintained at 18° C. for 18 hours. The cells were collected by centrifugation (10,000 rpm, 10 min, 4° C.), suspended with 30 ml of 50 mM Tris-HCl (pH 8.0) and 150 mM NaCl, and lysed by sonication. The crude extract was centrifuged (10,000 rpm, 30 min, 4° C.), and the supernatant was filtered through a 0.2 mm filter, and applied directly to the Ni FF chromatography of Example 3 below.

Example 3: Ni-NTA Purification

The supernatant of the lysate was loaded onto a 5 ml Ni-NTA (GE) column, and the column was washed with a 20-fold column volume of buffer A (50 mM Tris-Cl, pH 8.0, 150 mM NaCl, 30 mM imidazole and 5 mM BME), and then with a 5-fold column volume of buffer B (50 mM Tris-Cl, pH 8.0, 150 mM NaCl). After washing, an aliquot of the protein-bound resin was equilibrated with digestion buffer (buffer B containing 5 mM $CaCl_2$ and 5 mM tri-Gly), and then incubated at 25° C. for 1 hour.

The protein purity was analyzed by SDS-PAGE gel electrophoresis, and the molecular weight of the protein was analyzed by MALDI-TOF MS (mass spectroscopy). The protein yield was quantified by UV spectrophotometry at 280 nm with the calculated value.

Example 4: Pairing of $V_H$ and $V_L$ Domain Antibodies

The binding reaction of $V_H$ and $V_L$ domains into Fv heterodimers was performed by mixing the same volumes of $V_H$ and $V_L$. For pairing condition, 100 μg/ml of $V_H$ protein and 100 μg/ml of $V_L$ protein were mixed with each other in 50 mM Tris buffer (pH 8.0) and incubated at room temperature for 1 hour.

Figure 2:
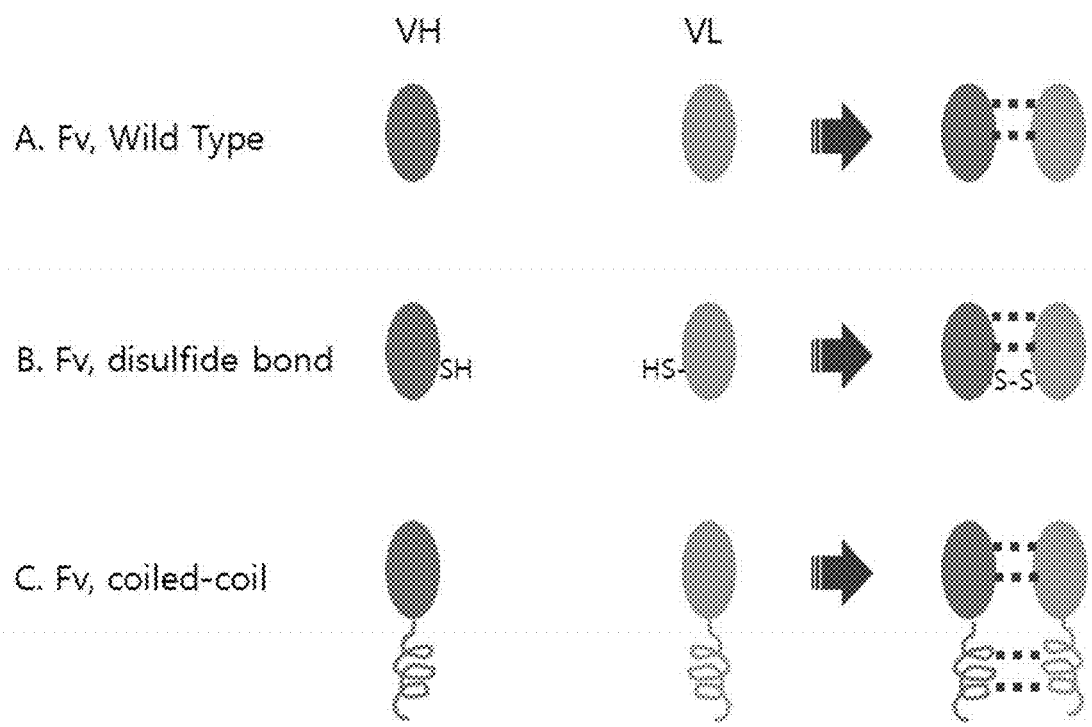
FIG. 2 schematically shows link by pairing for constructing an Fv library based on a combination of proteins according to the present invention. (A): paring between wild-types; (B): paring by disulfide bonds; and (C) paring by coiled-coil.

The binding between the $V_H$ and $V_L$ domains in the present invention is paring between wild-type domains, paring by a disulfide bond, or coiled-coil binding, and a schematic view of each binding method is shown in FIG. 2.

The assembled Fv was analyzed by ELISA and size exclusion chromatography, and the molecular weight of the protein was analyzed by MALDI-TOF MS. In addition, the Fv assembled by disulfide bond was analyzed by SDS-PAGE gel electrophoresis and ELISA.

Specifically, a microplate (Nunc, Maxisorp) was coated overnight with 300 ng antigen (Erbb2) and capture antibody in carbonate/bicarbonate buffer (pH 9.6) at 4° C. The plate was washed with 0.05% PBS-T, and then blocked with PBS-T containing 3% skimmed milk at 37° C. for 1 hour. The assembled Fv (1-0.5 gig) was added to the plate and incubated at 37° C. for 1 hour. The plate was washed and incubated with a 1:2500 dilution of horseradish peroxidase-conjugated anti-HA or myc antibody in PBS-T containing 3% skimmed milk. The plate was incubated at 37° C. for 1 hour, washed, and then developed with TMB (Sigma)/peroxidase substrate solution. The reaction was stopped with 2N $H_2SO_4$, and absorbance was read at 450 nm.

Example 5: HPLC Analysis

Size exclusion HPLC (high performance liquid chromatography) was performed with an Agilent 1260 series HPLC system having a diode array detector. The column (7.80×300 mm BioSep-SEC-s2000) was purchased from Phenomenex. 50 mM $KH_2PO_4$ and 100 mM KCl (pH 6.5) were used as a mobile phase.

Example 6: Collection of Antibody Sequences

PSI-BLAST was used to search a database of all sequences in the PDB, the non-redundant sequence file pdbaanr available on the PISCES website, using the variable domain regions of the antibody structure in PDB entry 1Q9R. Only sequences above 35% identity and E-value with better than $1.0 \times 10^{-20}$ were kept, such that only antibody domains remained (e.g., excluding T-cell receptors and other Ig sequences). The resulting heavy chain and light chain sequences were collected at 90% identity using the PISCES server. Multiple sequence alignments of the heavy chain sequences and of the light chain sequences were determined separately with Clustal W and manually collected and edited. These alignments were then used to create heavy and light chain specific hidden Markov models, using the program HMMER. A profile HMM is a statistical model of a multiple sequence alignment of a protein family, including position-specific insertion probabilities. This makes them well suited for determining the positions of the CDRs, which occur at well-defined positions within the variable domain sequences and which vary in length. These HMMs were used to search pdbaa (the set of all protein sequences in the PDB, including redundancy), available from the PISCES server (http://dunbrack.fccc.edu/PISCES.php). Cutoff values for HMMER scores and E-values were chosen such that when searching pdbaa protein sequences, only antibody heavy and light-chain sequences scored better than the cutoffs. Sequences found by both HMMs were assigned to the one with the higher score and smaller E-value. Both K and A light chains score better than the cutoffs for the light-chain HMM. These profile HMMs, one for the heavy chain and one for the A light chain, were further utilized to identify specific conserved framework positions before and after each CDR.

Example 7: CDR Analysis

An aligned collection of realigned antibody $V_H$ and $V_L$ sequences was used for analysis of the CDR length and composition. CDRs in each alignment were grouped according to the CDR length. Individual groups were classified as canonical structures according to Chothia et al., Conformations of immunoglobulin hypervariable regions. Nature. 1989; 342:877-883). All analyses were performed using Excel.

Example 8: Verification of Effective Fv Antibody Formation and Activity by Combination of Proteins Efficient Fv antibody formation and activity by the combination of proteins were verified by introducing mutations into $V_H$ and $V_L$ proteins using the well-known HERCEPTIN as a model.

Experimental Example 1: Confirmation of Simple Purification by Self-Cleavage of Fusion Protein It was confirmed that the target protein $V_H$ domain or $V_L$ domain can be simply separated from the fusion protein by the methods of Examples 1 to 3 above.

Specifically, for Flag-$V_H$-linker-coiled coil-HA-Flag-LPETG-linker (7, 18 or 20 a.a.)-SrtA-His10, the following sequences were used.

Specifically, Flag (DYKD: SEQ ID NO: 20), $V_H$ (EVQLVESGGGLVQPGGSLRLSCAASGFNIKDTYIHWVRQAPGKGLEWVARIYPTNGYTRYADSVK GRFTISADTSKNTAYLQMNSLRAEDTAVYYCSRWGGDGFYAMDYWGQGTLVTVSS: SEQ ID NO: 21), linker (SLEGTGGTSGSTSGTGGSSRSSST: SEQ ID NO: 22) and HA (YPYDVPDYAK: SEQ ID NO: 23) were used, and the coiled-coil sequences shown in Table 1 below were used.

TABLE 1

| Coiled-coil | Sequences | SEQ ID NO: |
|---|---|---|
| H1. winzipA1 | TVAQLEEKVKTLRAQNYELKSRVQRLREQVAQLASEFEL | 24 |
| H2. winzipA2 | TVAQLRERVKTLRAQNYELESEVQRLREQVAQLASEFEL | 25 |
| H3. Vel A1 | TVAQLEEKVKTLRAENYELKSEVQRLEEQVAQLASEFEL | 26 |
| H4.Max | TMRRKNDTHQQDIDDLKRQNALLEQQVRALASEFEL | 27 |
| H5. EE1234L | TLEIEAAFLEQENTALETEVAELEQEVQRLENIVSQYETRYGPLGGASEFEL | 28 |

TABLE 1-continued

| Coiled-coil | Sequences | SEQ ID NO: |
|---|---|---|
| H6.VSALE5 | TEVSALKEKVSALEKEVSALKEKVSALEKEVSALEKGGASEFEL | 29 |
| H7.VSALE3ox | TCGGEVSALEKEVSALEKEVSALEKASEFEL | 30 |
| H8.IAALE3 | TEIAALEKEIAALEKEIAALEKASEFEL | 31 |

Specifically, for $V_L$-linker-coiled coil-myc-LPETG-linker (7, 18 or 20 a.a.)-SrtA-His10, the following sequences were used.

$V_L$(DIQMTQSPSSLSASVGDRVTITCRASQDVNTAVAWYQQKPGKAPKLLIYSASFLYSGV PSRFSGSRSGTDFTLTISSLQPEDFATYYCQQHYTTPPTFGQGTKVEIK: SEQ ID NO: 32), linker (ALEGTGSST GSS TGPGGSSRSSST: SEQ ID NO: 33) and myc (EQKLISEEDLKLPET: SEQ ID NO: 34) were used, and the coiled-coil sequences shown in Table 2 below were used.

TABLE 2

| Coiled-coil | Sequences | SEQ ID NO: |
|---|---|---|
| L1. wizipB1 | SVDELQAEVDQLQDENYALKTKVAQLRKKVEKLASEFEL | 35 |
| L2. winzipB2 | GPGGSSRSSSTSVDELKAEVDQLQDQNYALRTKVAQLRKEVEKLSEEFEL | 36 |
| L3. Vel B1 | GPGGSSRSSSTSVDELQAEVDQLEDENYALKTKVAQLRKKVEKLASEFEL | 37 |
| L4. myc | GPGGSSRSSSTSVQAEEQKLISEEDLLRKRREQLKHKLEQLASEFEL | 38 |
| L5. RR1234L | GPGGSSRSSSTSKGGGLEIRAAFLRRRNTALRTRVAELRQRVQRLRNIVSQYETRYGPASFEEL | 39 |
| L6. VSALK5 | GPGGSSRSSSTKVSALKEKVSALKEKVSALKEKVSALKEKVSALKEGGEFEL | 40 |
| L7. VSALk3ox | GPGGSSRSSSTCGGKVSALKEKVSALKEKVSALKEGGEFEL | 41 |
| L8.IAALK3 | GPGGSSRSSSTSKIAALKEKIAALKEKIAALKEASEFEL | 42 |

The sequence of Flag-$V_H$ (H-G44C or H-Q105C)-HA-Flag-LPETG-linker (7, 18 or 20 a.a.)-StrA-His10 having a cysteine mutation introduced therein was the same as described above except for the $V_H$ shown in Table 3 below.

TABLE 3

| CYS MUTANTS | Sequences | SEQ ID NO: |
|---|---|---|
| C1. H-G44C | EVQLVESGGGLVQPGGSLRLSCAASGFNIKDTYIHWVRQAPGKCLEWVARIYPTNGYTRYADSVKGRFTISADTSKNTAYLQMNSLRAEDTAVYYCSRWGGDGFYAMDYWGQGTLVTVSSYPYDVPDYA | 43 |
| C2. H-Q105C | EVQLVESGGGLVQPGGSLRLSCAASGFNIKDTYIHWVRQAPGKGLEWVARIYPTNGYTRYADSVKGRFTISADTSKNTAY | 44 |

TABLE 3-continued

| CYS MUTANTS | Sequences | SEQ ID NO: |
|---|---|---|
| | LQMNSLRAEDTAVYYCSRWGGDGFYAMDYWGCGT LVTVSSYPYDVPDYA | |

The sequence of $V_L$ (L-A43C or L-Q100C)-MYC-LPETG-linker (7, or 20 a.a.)-StrA-His10 having a cysteine mutation introduced therein was the same as described above except for the $V_L$ shown in Table 4 below.

TABLE 4

| CYS MUTANTS | Sequences | SEQ ID NO: |
|---|---|---|
| C3. L-A43C | DIQMTQSPSSLSASVGDRVTITCRASQDVNTAVAWY QQKPGKCPKLLIY SASFLYSGVPSRFSGSRSGTDFTLTISSLQPEDFAT YYCQQHYTTPPTFGQGTKVEIKEQKLISEEDL | 45 |
| C4. L-Q100C | DIQMTQSPSSLSASVGDRVTITCRASQDVNTAVAWY QQKPGKAPKLLIYSASFLYSGVPSRFSGSRSGTDFT LTISSLQPEDFATYYCQQHYTTPPTFGCGTKVEIKE QKLISEEDL | 46 |

Figure 3:
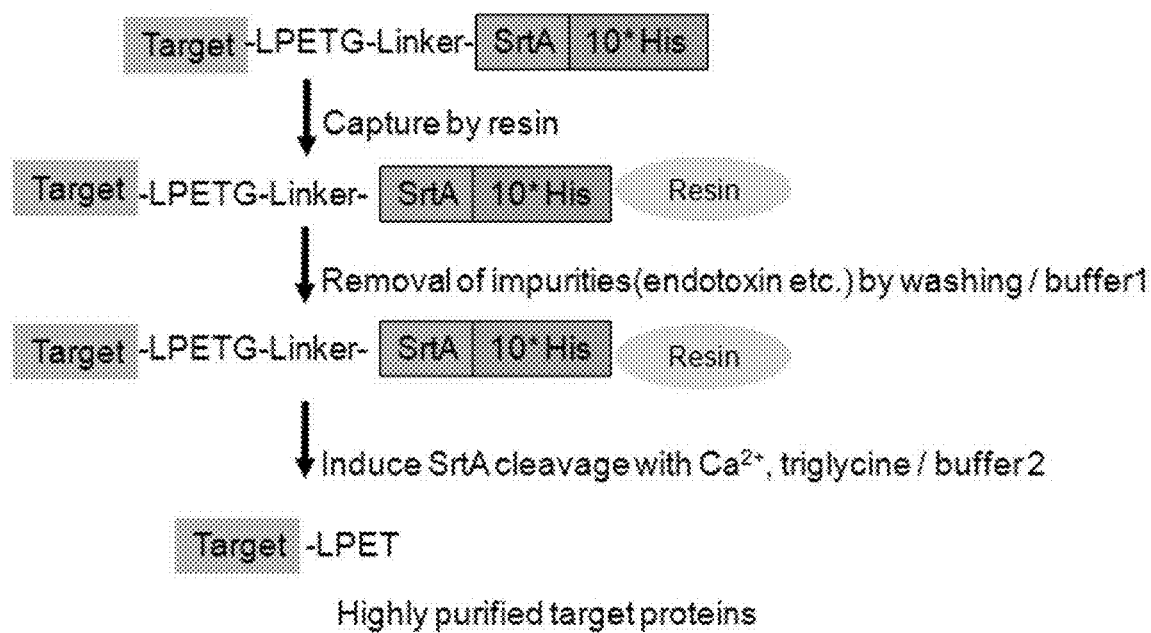
FIG. 3 schematically shows a simple protein purification process.

This simple purification method is schematically shown in FIG. 3.

Figure 4:
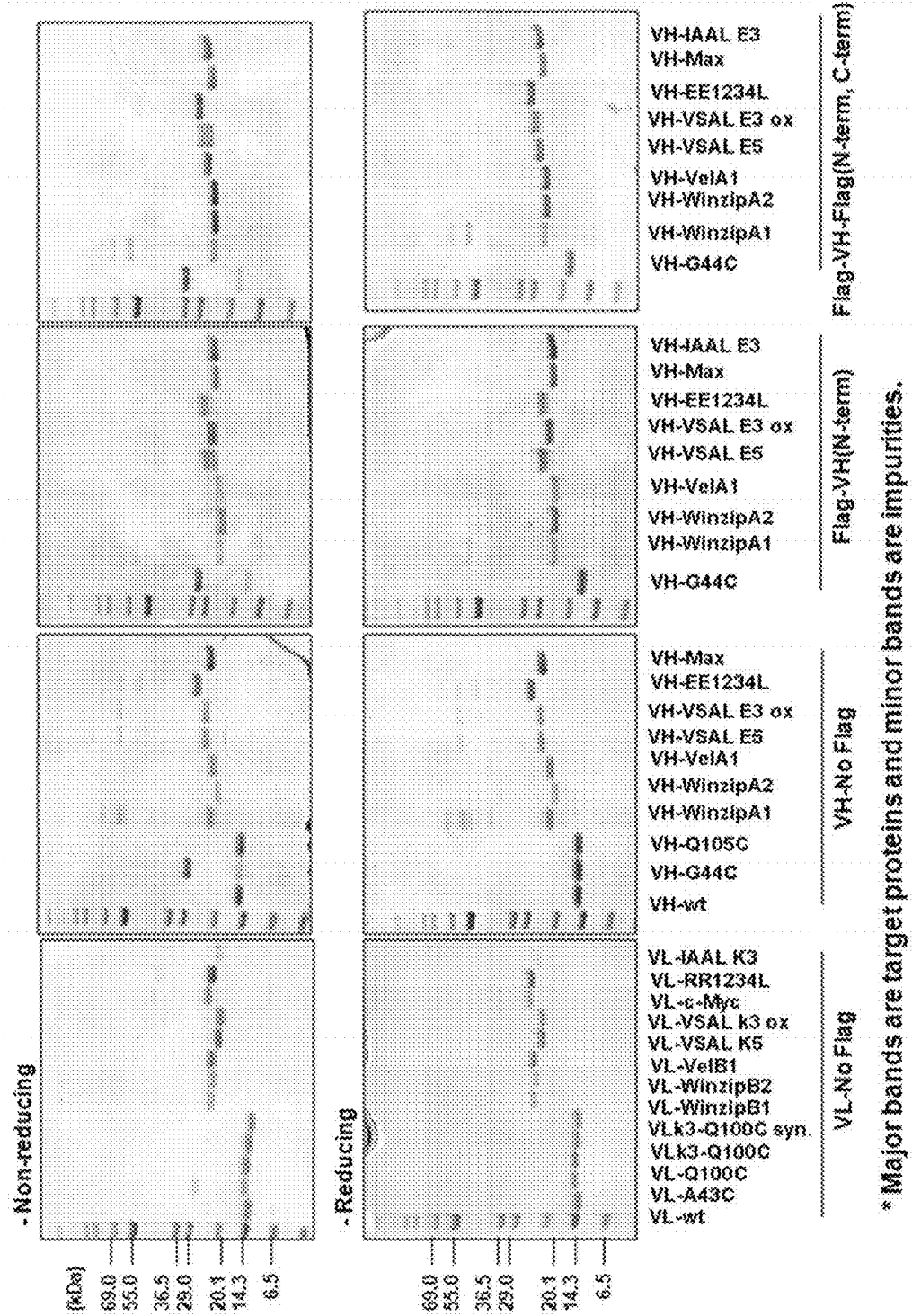
FIG. 4 shows the results of SDS-PAGE of purified $V_L$ and $V_H$ mutants.
Figure 5:
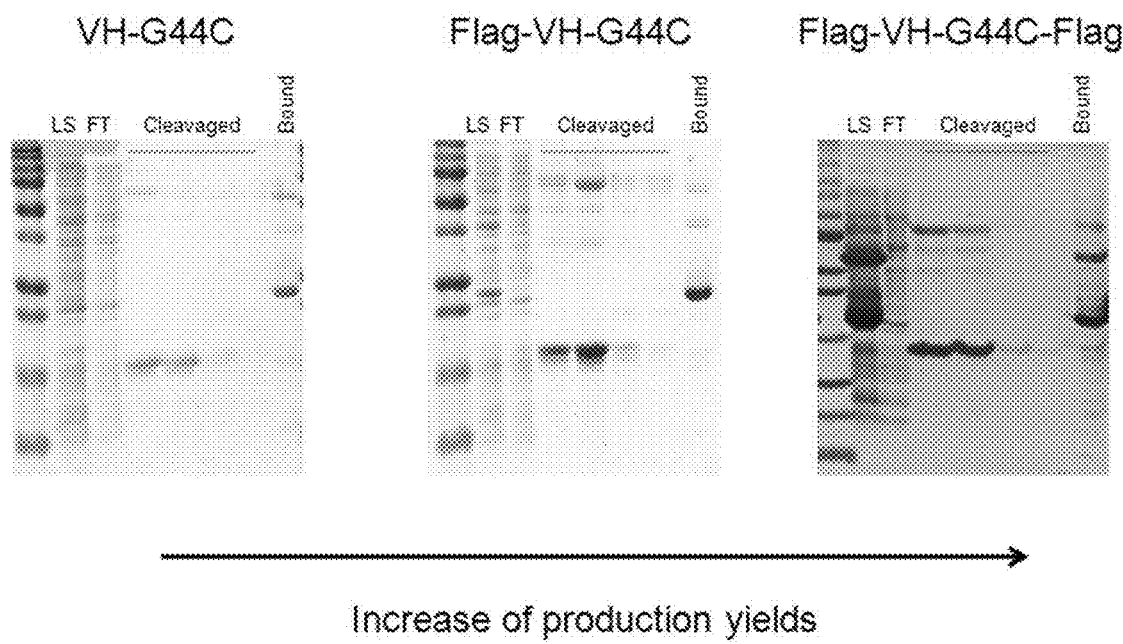
FIG. 5 shows that the expression of $V_H$-G44C that is a $V_H$ domain protein having no Flag tag, Flag-$V_H$-G44C having a Flag tag at the N-terminus, and Flag-$V_H$-G44C-Flag protein having a Flag tag at the N-terminus and C-terminus, increases in the presence of the Flag tag.

The results of SDS-PAGE of the $V_L$ and $V_H$ purified by the method of FIG. 3 are shown in FIG. 4. In addition, FIG. 5 shows the yield of purification by Flag tag. Such results are summarized in FIG. 6.

Information on the sequences shown in FIG. 4 was obtained from the BLAST database (http://blast.ncbi.nlm.nih.gov/Blast.cgi). The sequences shown in FIGS. 3 and 4 were randomly mutated by introducing cysteines into the interface between the heavy-chain variable region and light-chain variable region of 4D5 (HERCEPTIN®) to form heterodimers.

As a result, the purification yield of $V_L$ in the non-fusion system was 10 mg/l, and the purification yield of $V_H$ was 0.2 mg/l. Thus, it was shown that the purification yield increased by about 3-6.5 times when the Sortase fusion method designed by the present inventors was used (FIG. 6). In addition, it was shown that the expression level increased by about 2-55 times when Flag tag was used (FIG. 6).

Figure 7:
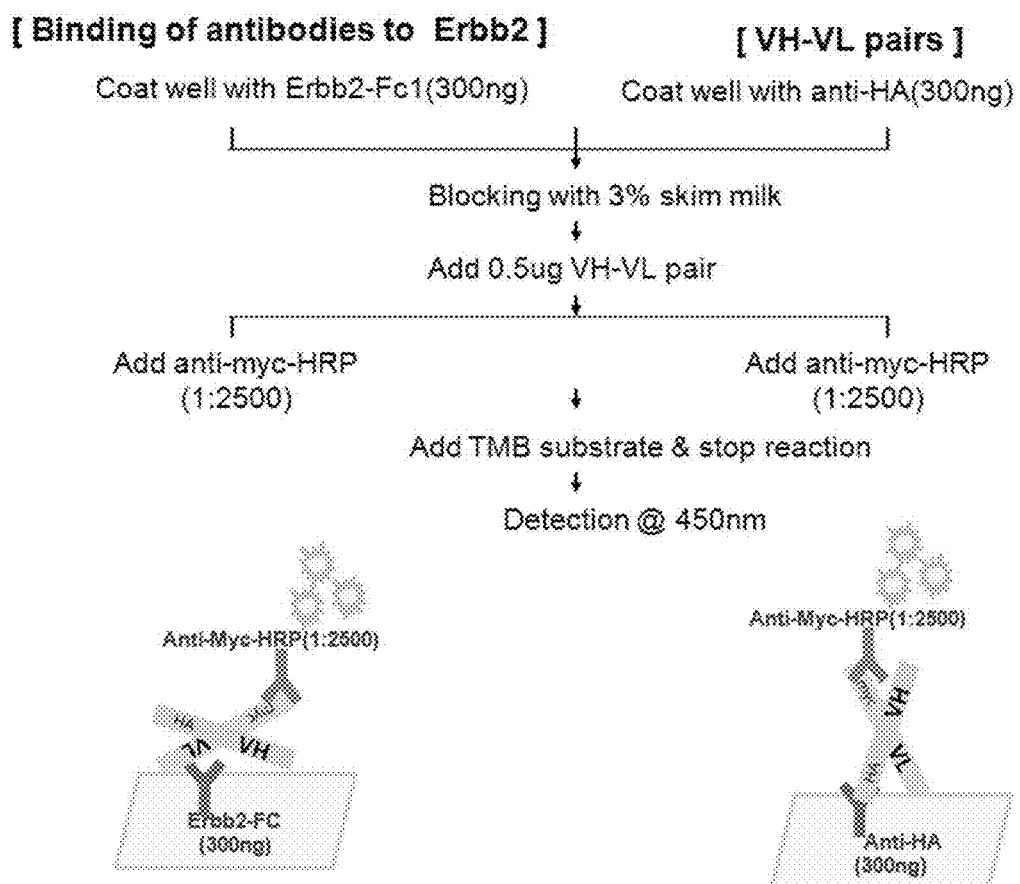
FIG. 7 is a schematic view showing a method of on analyzing link of $V_H$-$V_L$ by pairing.

Experimental Example 2: Analysis of Pairs at Protein Level by ELISA Assay $V_H$-$V_L$ pairs were analyzed by ELISA according to the method of Example 4. FIG. 7 schematically shows this ELISA method.

Figure 8:
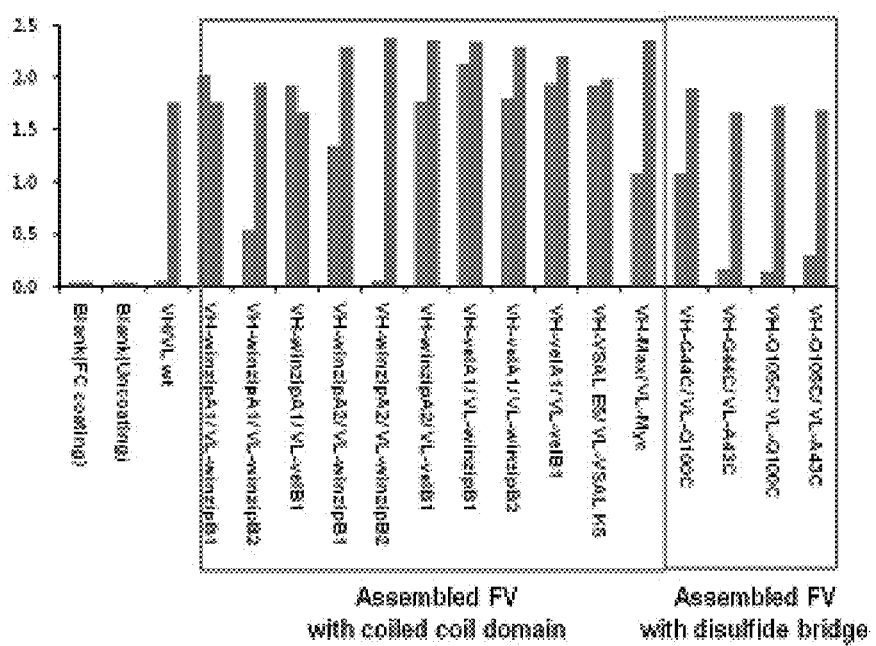
FIG. 8 shows the ELISA results of analyzing pairing of $V_H$-$V_L$.

Specifically, $V_H$-HA tag and $V_L$-myc tag were designed, and a total of 16 pairs, including one wild-type pair (wt), 11 pairs with coiled-coil domains and 4 pairs with disulfide bonds, were analyzed by ELISA assay. The results of ELISA of the $V_H$-$V_L$ pairs are shown in FIG. 8. As a result, it was shown that all the pairs were observed at similar levels when they did bind to antigens. When analysis was performed with anti-HA-pairs-anti-myc HRP without antigen, the wild-type showed no signal, and among 11 parings with coiled-coil domains, $V_H$ winzipA1/$V_L$ winzipB2 showed a low signal, and $V_H$ winzipA2/$V_L$ winzipB2 showed no signal. Among 4 pairs with disulfide bonds, only $V_H$ G44C/$V_L$ Q100C showed a signal (FIG. 8, light bar: anti-HA/Fv/anti-myc HRP, right bar: Erbb2/Fv/anti-myc HRP).

Figure 9:
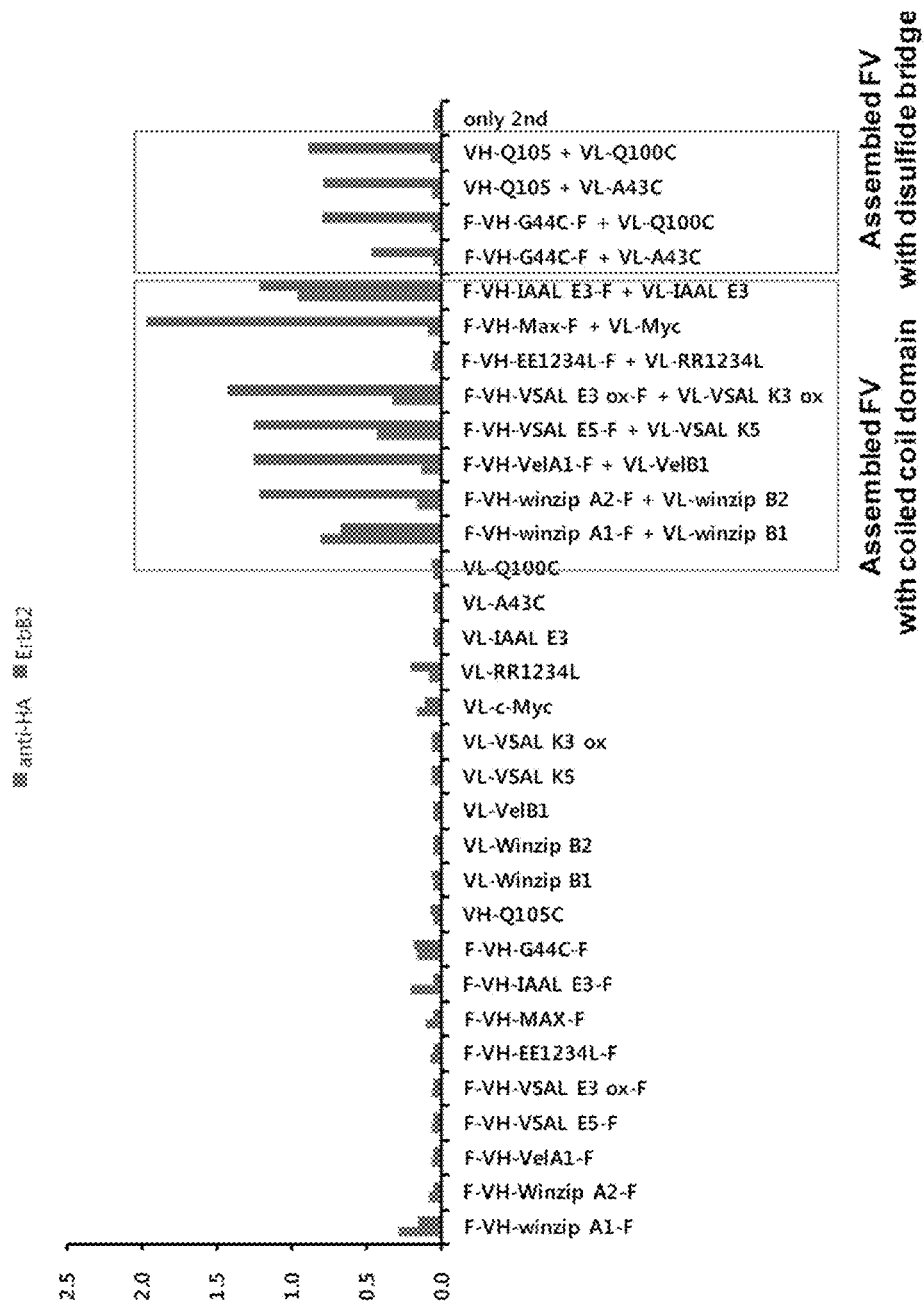
FIG. 9 shows the ELISA results of analyzing pairing of Flag-$V_H$ and Flag-$V_L$.

In addition, Flag-tagged $V_H$ and $V_L$ were designed, and a total of 12 pairs, including 8 pairs with coiled-coil domains and 4 pairs with disulfide bonds, were analyzed by ELISA. As a result, it was shown that all the pairs were observed at similar when they did bind to antigens. When analysis was performed with anti-HA-pairs-anti-myc HRP without antigen, $V_H$ winzipA1/$V_L$ winzipB1 and $V_H$ IAAL E3/$V_L$ IAAL K3 among eight pairs with coiled-coil domains showed high signals. In addition, four pairs with disulfide bonds showed no signal in ELISA, but showed pairing in other assays (SDS-PAGE, MALDI-TOF-MS, etc.) (FIG. 9).

The above results support that the protein $V_H$ and $V_L$ domains of the present invention can provide an Fv library having diversity by random pairing.

Figure 10:
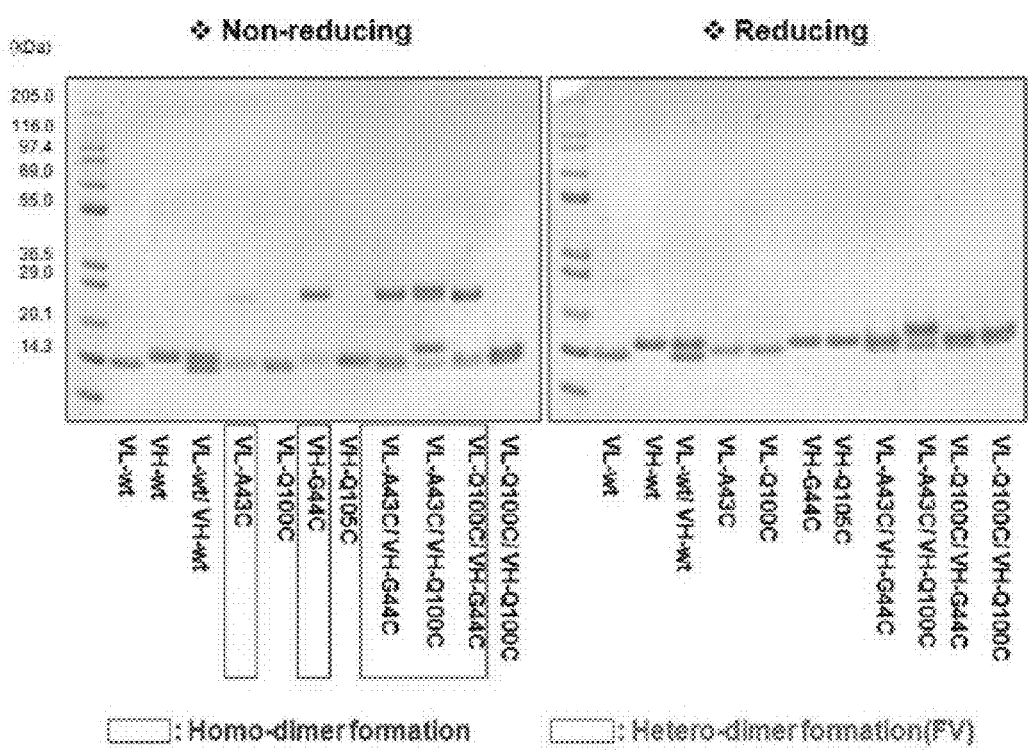
FIG. 10 shows the results of SDS-PAGE on pairing of $V_H$-$V_L$, in which cysteine mutations are introduced.

Experimental Example 3: Analysis of $V_H$-$V_L$ Pairs at Protein Level by SDS-PAGE Analysis $V_H$-$V_L$ pairs were analyzed by SDS-PAGE according to the method of Example 4. FIG. 10 shows $V_H$-$V_L$ pairs with disulfide bonds formed between cysteine mutations introduced into $V_L$ and $V_H$. As a result, it was shown that $V_L$-Q100C/$V_H$-G44C, $V_L$-A43C/$V_H$-Q100C and $V_L$-A43C/$V_H$-G44C were paired by disulfide bonds to form heterodimers (FIG. 10).

Figure 11:
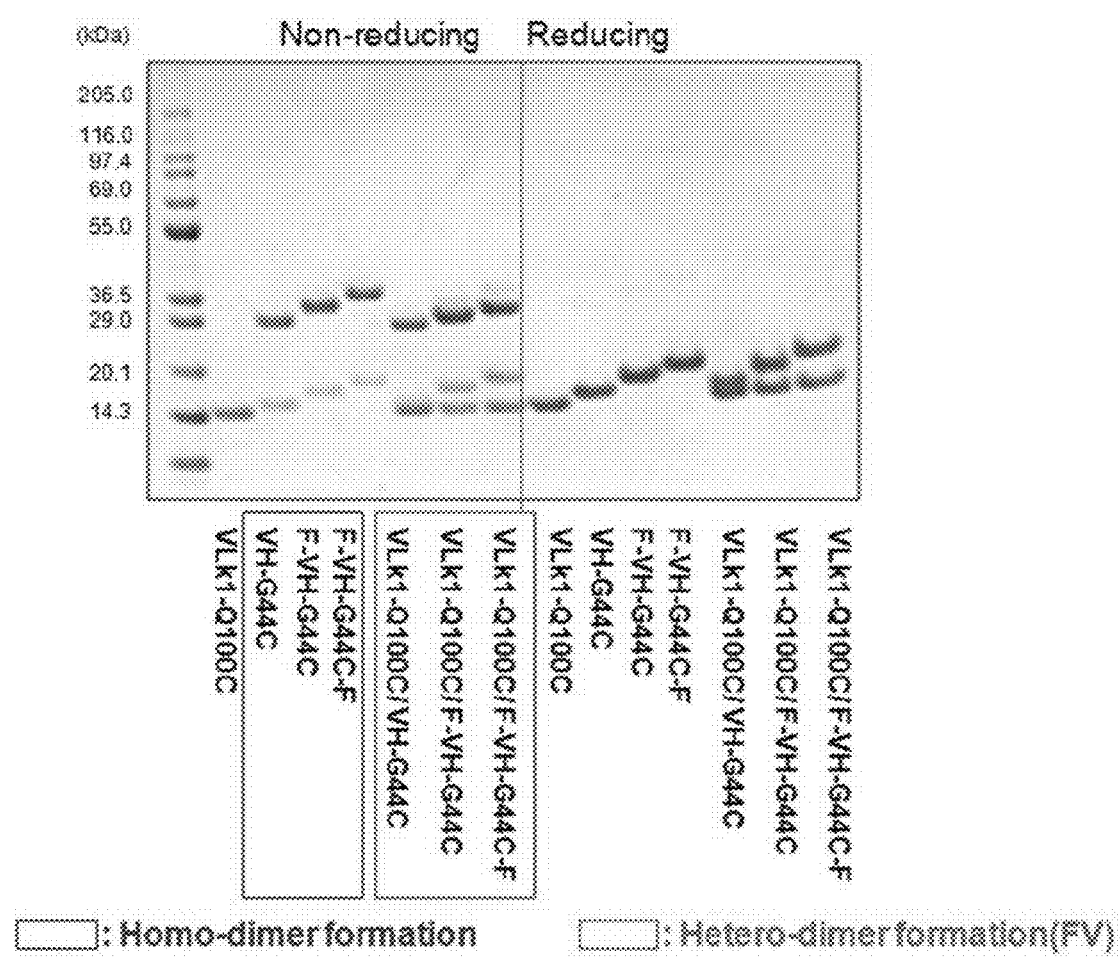
FIG. 11 shows SDS-PAGE results indicating that the pairing of Flag-$V_H$ and Flag-$V_L$ increases the pairing of $V_H$ and $V_L$.

Also, among $V_H$-$V_L$ pairs with the disulfide bonds formed by cysteine mutations introduced into $V_L$ and $V_H$, $V_H$-$V_L$ pairs with disulfide bonds between Flag-$V_H$ and $V_L$ are shown in FIG. 11. As a result, it was shown that $V_L$k1-Q100C/F-$V_H$-G44C-F, $V_L$k1-Q100C/F-$V_H$-G44C and $V_L$k1-Q100C/$V_H$-G44C were paired by disulfide bonds to form heterodimers and showed increased production rate (FIG. 11).

The above results support that the protein $V_H$ and $V_L$ domains of the present invention can provide an Fv library having diversity by random pairing.

Experimental Example 4: Analysis of $V_H$-$V_L$ Pairs at Protein Level by SEC-HPLC Analysis $V_H$-$V_L$ pairs were analyzed by size exclusion chromatography (SEC-HPLC) according to the methods of Examples 4 and 5.

Figure 12:
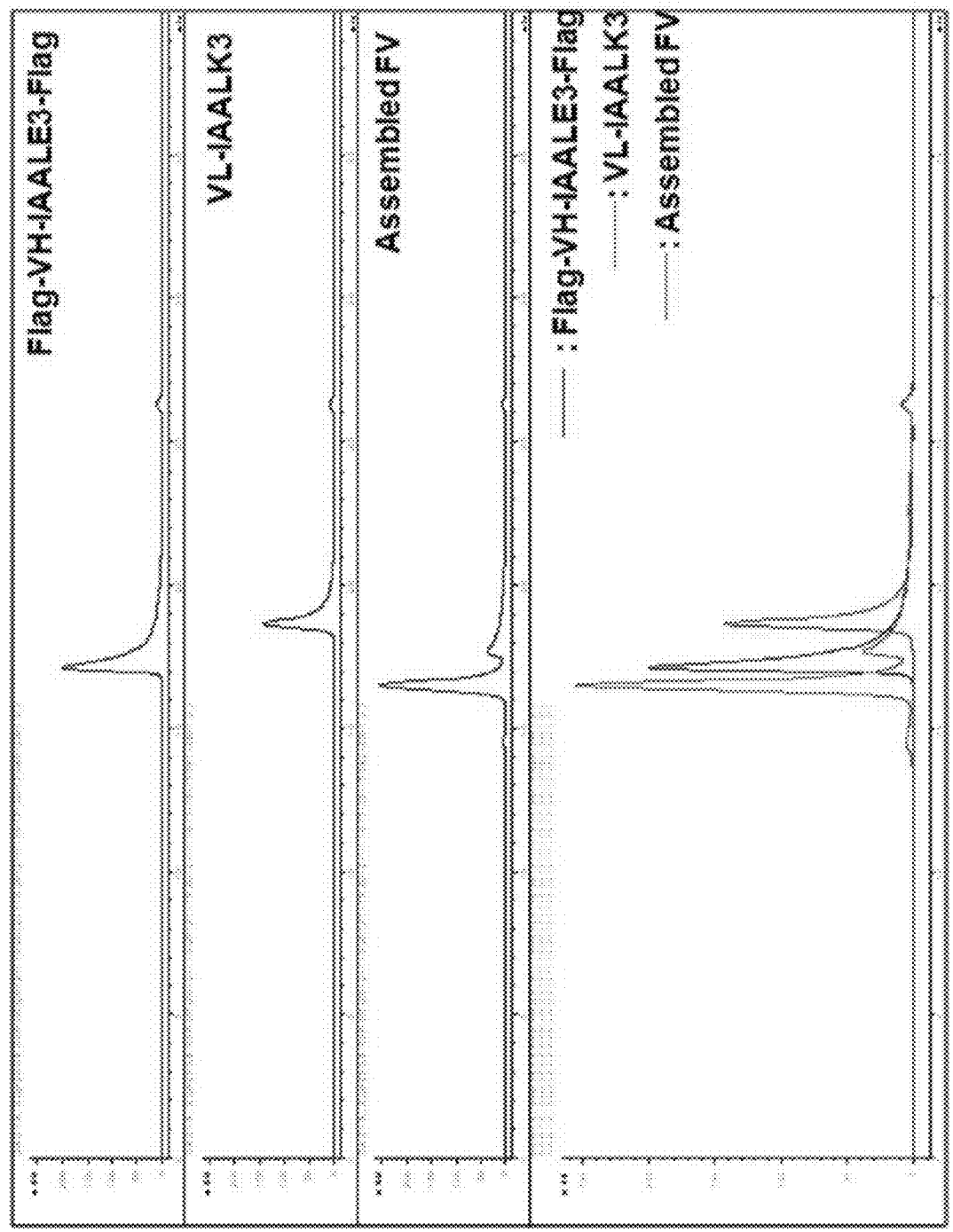
FIG. 12 shows the results of SEC-HPLC of $V_L$-IAALK3, Flag-$V_H$-IAALE3-Flag and assembled Fv.

The conditions of the SEC-HPLC are as follows:
Column: 7.80×300 mm BioSep-SEC-s2000
Mobile phase: PBS, pH 7.4
Column flow rate: 0.5 ml/min
Column temperature: 25° C.
UV absorbance detector: 280 nm, 210 nm
Injection volume: 100 μl FIG. 12 shows the results of size exclusion chromatography of $V_L$-IAALK3, Flag-$V_H$-IAALE3-Flag and assembled Fv.

Specifically, Flag-tagged $V_H$-HA tag and $V_L$-myc tag were designed, and a total of 16 pairs, including one wild-type pair (wt), 11 pairs with coiled-coil domains and 4 pairs with disulfide bonds, were analyzed by size exclusion chromatography. FIG. 12 shows the results of size exclusion chromatography of $V_L$-IAALK3, Flag-$V_H$-IAALE3-Flag and assembled Fv. As a result, it was shown that assembled Fv, Flag-$V_H$-IAALE3-Flag and $V_L$—IAALK3 were detected in this order.

In other results for $V_L$-IAALK3, Flag-$V_H$-IAALE3-Flag and assembled Fv, including the wild-type pair, $V_H$ or $V_L$ was not detected, and assembled Fv showed a size in the size of molecular weight compared to $V_H$ or $V_L$ and was detected early. The $V_H$ or $V_L$ single domain antibody was difficult to analyze, due to high hydrophobicity known as the characteristic of the antibodies, most of the assembled Fvs were detected while highly hydrophobic residues exposed to the surface of each single domain antibody were hidden by the assembled Fv and changed into hydrophilicity. The above results support that the protein $V_H$ and $V_L$ domains of the present invention can provide an Fv library having various diversity by pairing.

Experimental Example 5: Analysis of Molecular Weight of $V_H$-$V_L$ Pairs by MALDI-TOF MS Analysis The molecular weights of $V_H$-$V_L$ pairs were analyzed by MALDI-TOF MS according to the methods of Examples 4 and 5.

Figure 13:
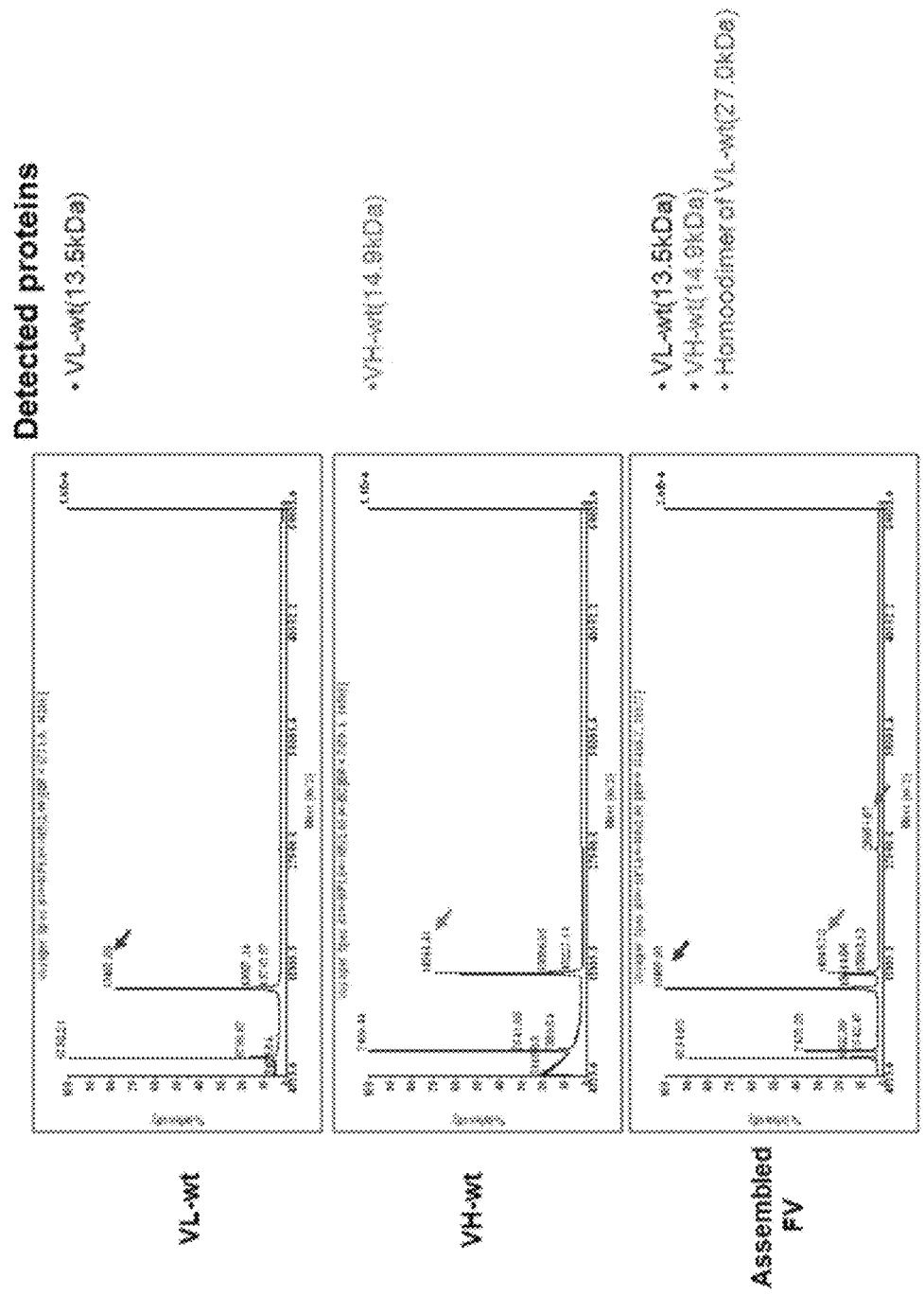
FIG. 13 shows the results of MALDI-TOF analysis of $V_L$, $V_H$ and assembled Fv wild-type.
Figure 14:
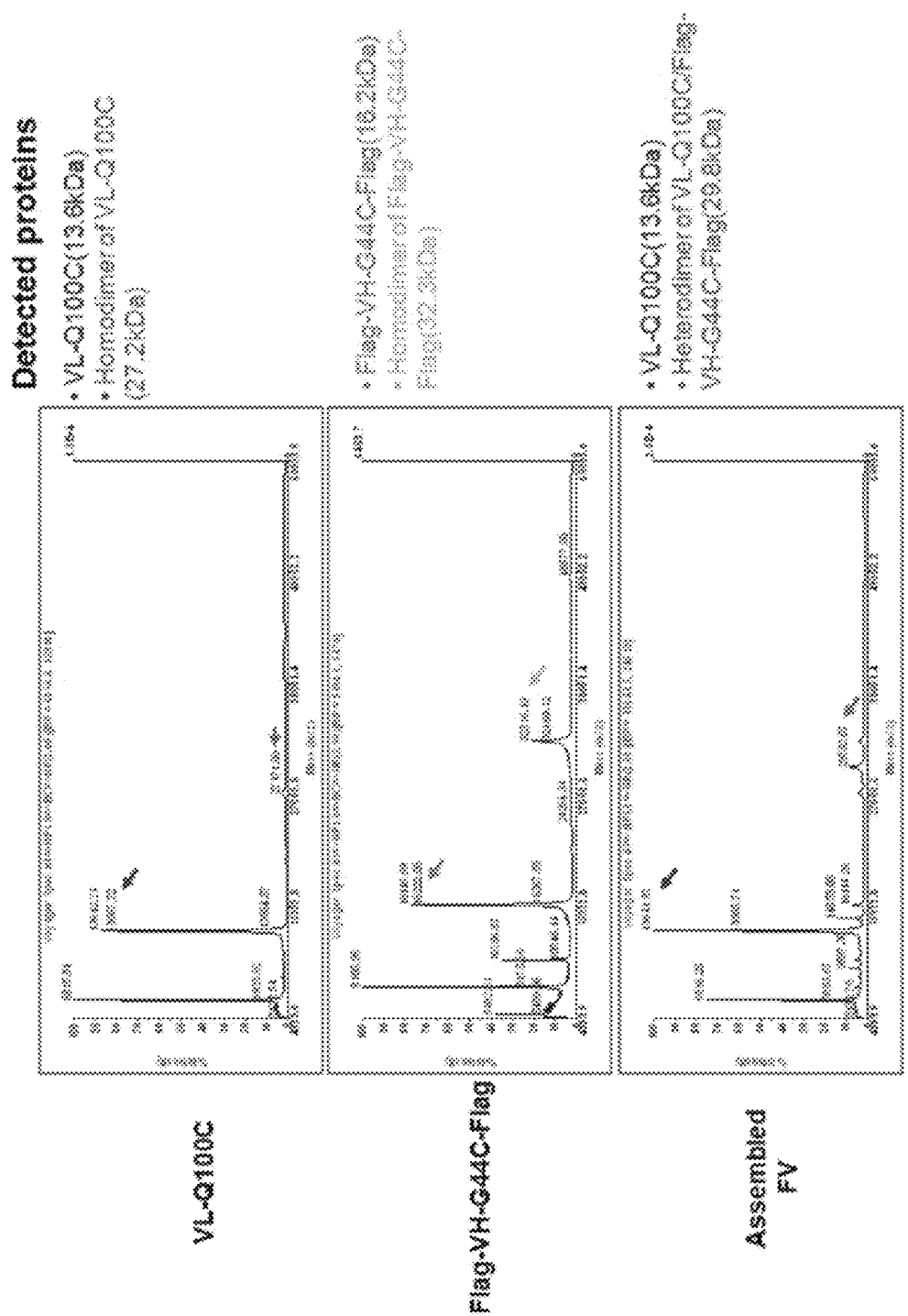
FIG. 14 shows the results of MALDI-TOF analysis of $V_L$-Q100C, Flag-$V_H$-G44C-Flag and assembled Fv.

FIG. 13 shows the results of analyzing the molecular weights of $V_L$, $V_H$ and Fv, FIG. 14 shows the results of analyzing the molecular weights of $V_L$-Q100C, Flag-$V_H$-G44C-Flag and Fv, and FIG. shows the results of analyzing the molecular weights of $V_L$-IAALK3, Flag-$V_H$-IAALE3-Flag and Fv.

Figure 15:
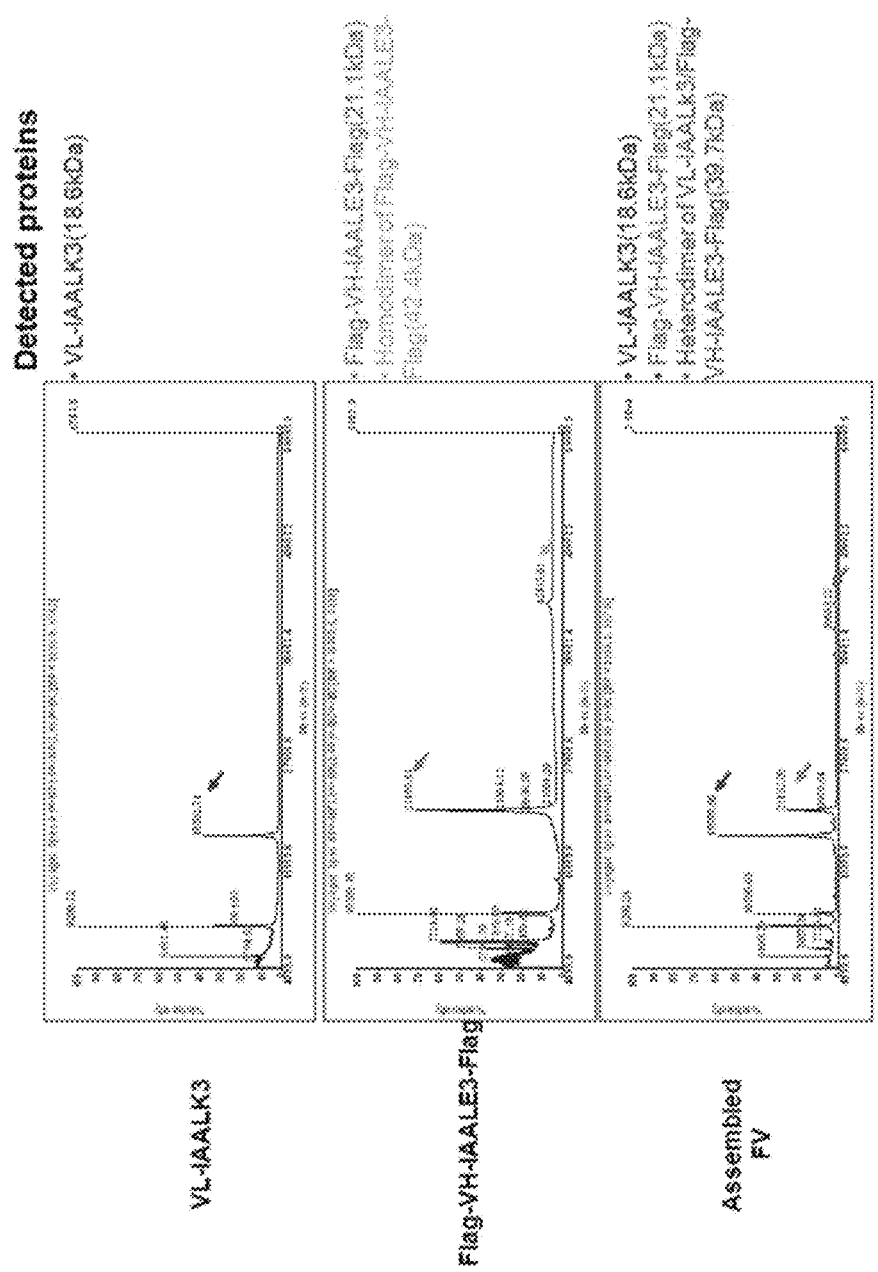
FIG. 15 shows the results of MALDI-TOF analysis of $V_L$-IAALK3, Flag-$V_H$-IAALE3-Flag and assembled Fv.

As a result, the molecular weight of each of $V_L$ and $V_H$ for wt could be accurately determined, and the molecular weight of assembled Fv was not determined (FIG. 13). Pairing could be confirmed based on the molecular weights of $V_L$-Q100C (13.6 kDa), Flag-$V_H$-G44C-Flag (16.2 kDa) and Fv (29.8 kDa) (FIG. 14). In addition, pairing could be confirmed based on the molecular weights of $V_L$-IAALK3 (18.6 kDa), Flag-$V_H$-IAALE3-Flag (21.2 kDa) and Fv (39.8 kDa) (FIG. 15).

Figure 16:
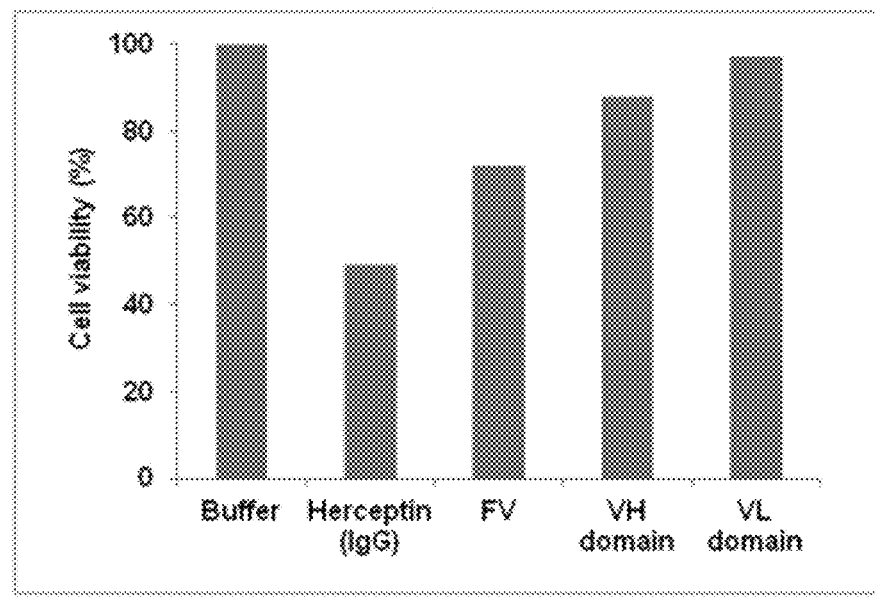
FIG. 16 shows the results of analyzing the effect of 4D5 Fv antibody on the proliferation of BT-474 cells by CCK8 assay (Dojjindo).

Experimental Example 6: Verification of Activity of Assembled Fv at Cellular Level The effect of 4D5 Fv antibody on the growth of BT-474 cells was analyzed by CCK8 assay (Dojjindo), and the results of the analysis are shown in FIG. 16. As can be seen in FIG. 16, human breast cancer BT-474 cells overexpress HER-2 on the surface thereof, and the growth of BT-474 was reduced by assembled 4D5 $F_V$ to an extent similar to that reduced by 4D5 IgG antibody.

After labeling with indirect immunofluorescence, the expression level of Her2 on the cell surface was analyzed by FACS sequentially using 4D5 IgG and FITC-conjugated anti-human-Fc. The binding of each of the $V_H$ domain, $V_L$ domain and assembled $F_V$ antibodies to BT-474 cells was confirmed by labeling the cells with 1 μg of anti-c-Myc antibody for 1 hour, and then labeling the cells with Alexa 488-conjugated anti-mouse antibody, followed by FACS.

Figure 17:
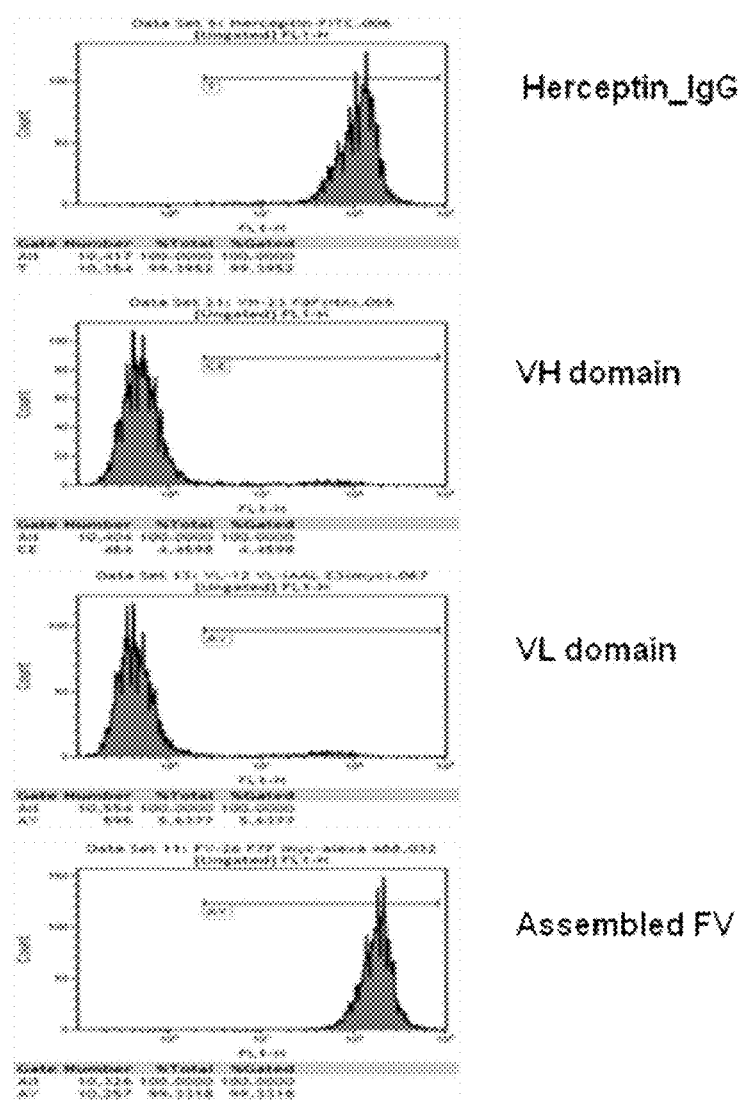
FIG. 17 shows the results of monitoring the profiles of binding of 4D5 IgG, $V_H$ domain, $V_L$ domain and assembled $F_V$ antibodies to the Her2-expressing cell surface of BT-474 cells by FACS.

The profiles of binding of 4D5 IgG, the $V_H$ domain, $V_L$ domain and assembled $F_V$ antibodies to the Her2-expressing cell surface of the BT-474 cells were monitored by FACS, and the results are shown in FIG. 17. The results of analysis with commercially available 4D5 IgG (positive control) indicated that HER-2 was overexpressed in BT-474 cells.

Experimental Example 7: Library Design

A functional combinatorial protein library constructed by pairing of $V_H$ and $V_L$ proteins was designed with a well-known antigen-antibody conjugate. A natural immune repertoire can generate antibodies that recognize essentially any antigen with high specificity and affinity. Antigen recognition is mediated by six complementarity determining regions (CDRs) that present a large surface for contact with antigen. CDR sequences are hypervariable, but the overall composition of functional CDRs is biased in favor of certain amino acid types. In the library of the present invention, functional diversity was restricted to small subsets of functional groups that are particularly well suited for mediating molecular recognition. The library of the present invention was generated by introducing high-frequency sequences important for formation of antigen-antibody complexes into the heavy-chain and light-chain CDR3 of each key antibody of the selected framework ensuring reliable folding and high expression yields. All CDR lengths were fixed at high frequency from collected antibodies. The compositions of CDR 1 and 2 were designed with the most abundant residues of collected antibodies. The library of the present invention had a combined complexity of $10^4$ antibodies by pairing of $V_H$ (100) and $V_L$ (100). The $V_{H3}$, $V_{Lk3}$ and $V_{Lk1}$ segments of human germline are found in antibodies rearranged at very high frequency and are easily expressed and paired.

The present inventors synthesized CDR1, CDR2 and CDR3 DNA sequences in the $V_{H3-66}$ and $V_{Lk1}$ framework, and introduced diversity into CDR-H3 and CDR-L3 using high-frequency sequences important for formation of antigen-antibody complexes.

Library design was performed according to the methods of Examples 6 to 8. As the framework, $V_{H3-66}$ and $V_{LK3}$ were used. Most of the heterodimers were HV3, HV1, HV4, KV3 and KV1.

Figure 18:
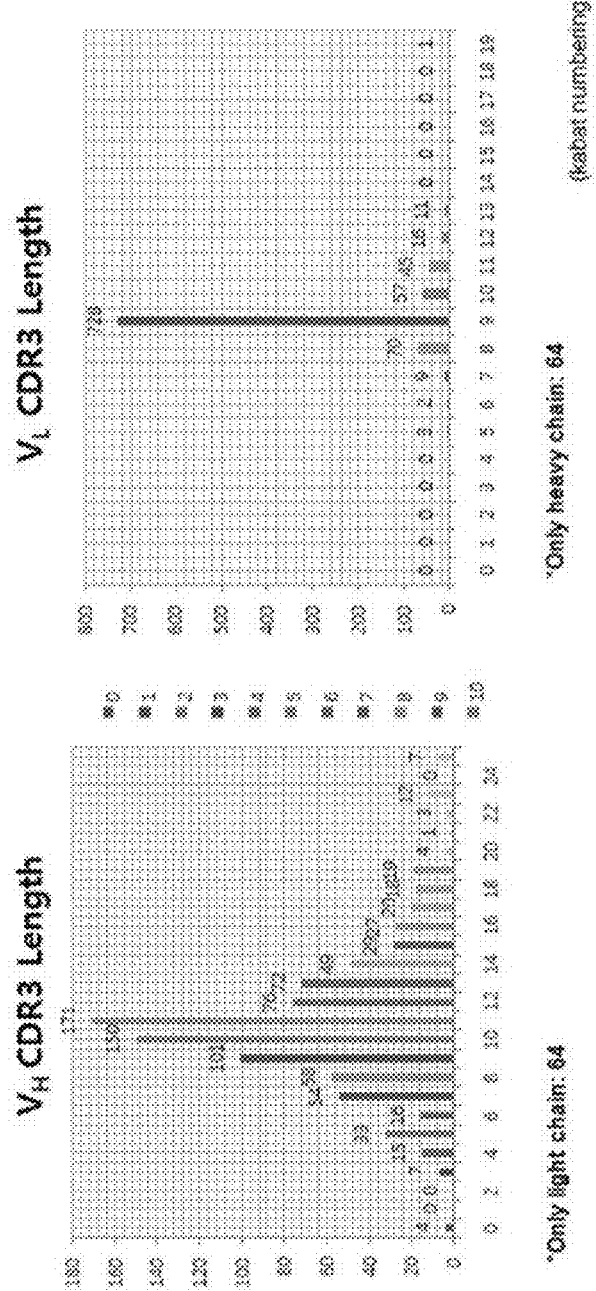
FIG. 18 shows the selection scheme of $V_H$ CDR3 and $V_L$ CDR3 for CDR design according to length distribution of amino acid residue.

The lengths of CDRs appearing at high frequency were set. Specifically, CDR H1 was fixed at a length of 10 amino acids; CDR H2 was fixed at a length of 10 amino acids; CDR H3 was fixed at a length of 11 amino acids; CDR L1 was fixed at a length of 11 amino acids; CDR L2 was fixed at a length of 7 amino acids; and CDR L3 was fixed at a length of 9 amino acids. The typical contents of CDR H3 and CDR L3 appearing at high frequency are shown in FIG. 18.

Experimental Example 8: Library Construction

Figure 19:
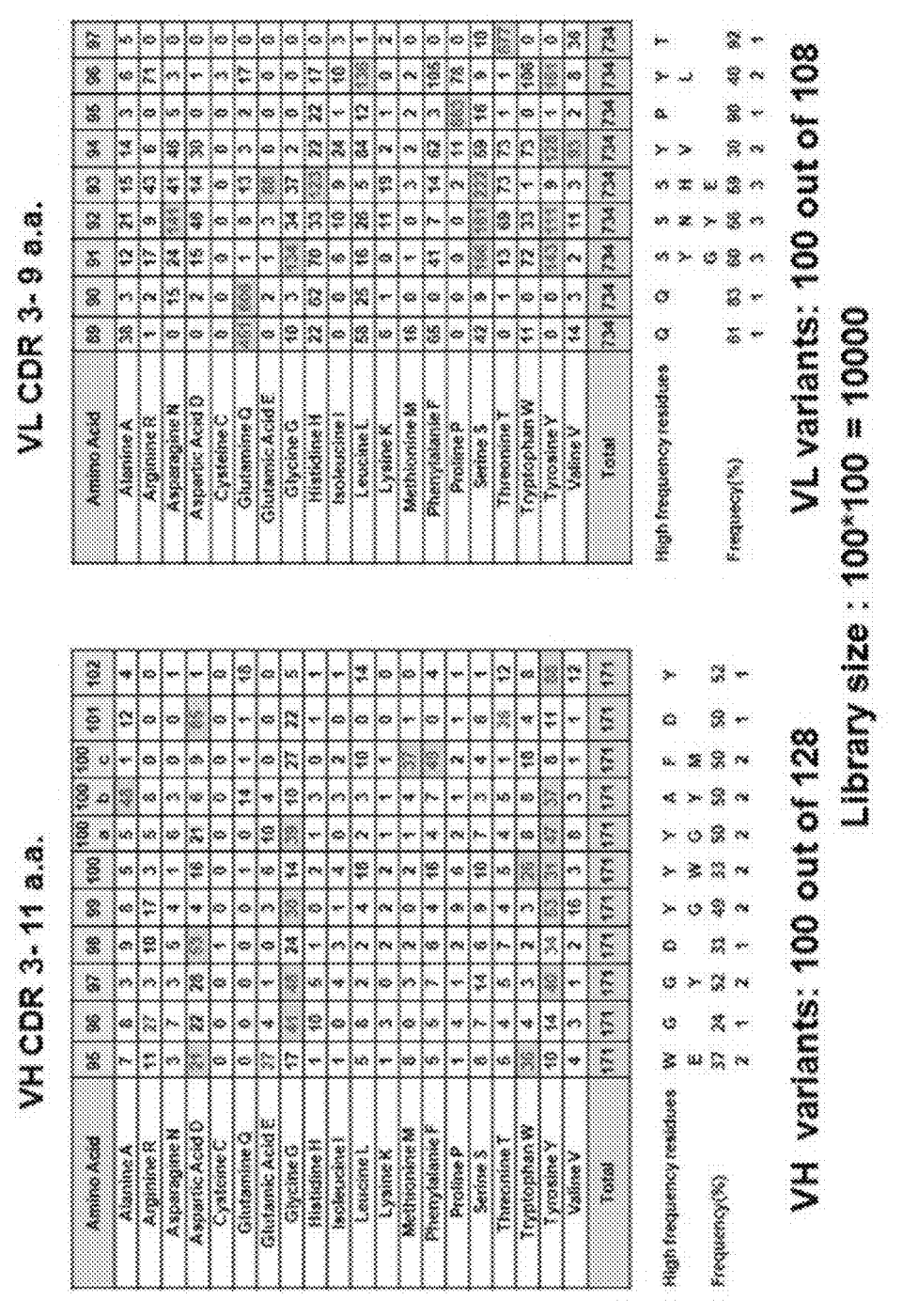
Figure 21:
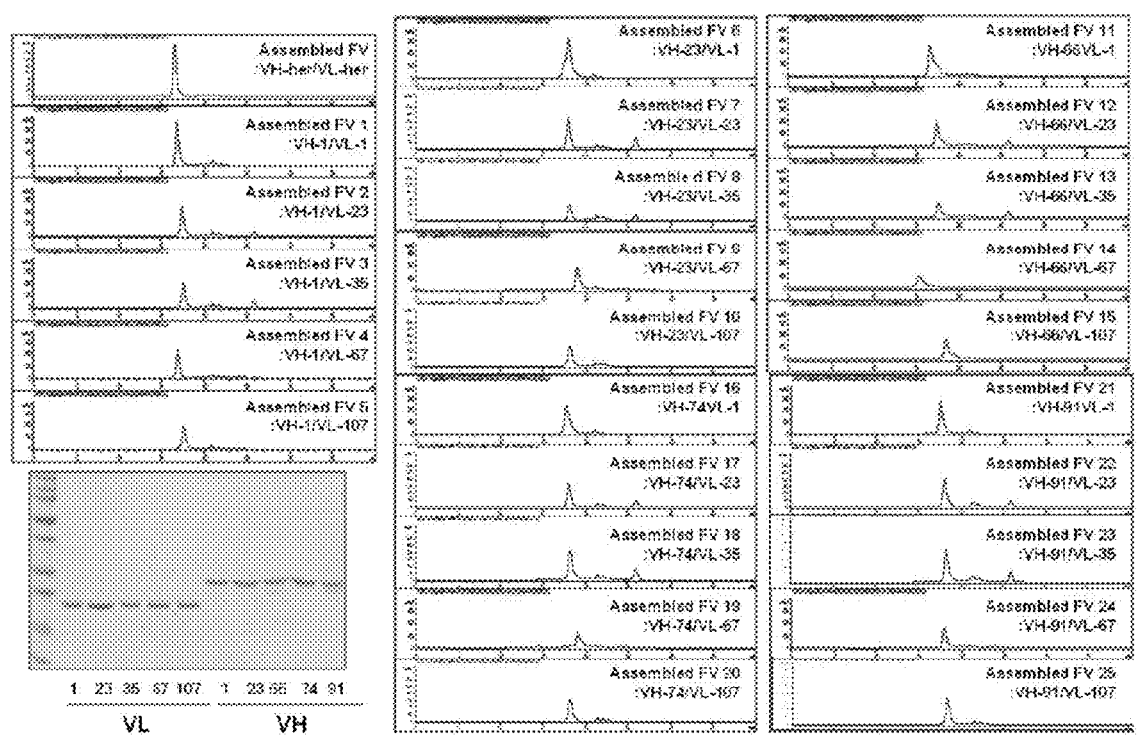
FIG. 21 shows the results of SEC-HPLC analysis of 25 $F_V$s constructed by combining 5 $V_H$s with 5 $V_L$s.

For diversity design, CDR1 and CDR2 were fixed with residues having the highest residues, and CDR3 was designed with high-frequency residues. An example thereof is shown in FIG. 19. 100 $V_H$ domains and 100 $V_L$ domains were combined to design a library having a diversity of 100×100=10000. The results are shown in FIG. 20. Among 10,000 $F_V$s constructed by the combination of proteins, 25 $F_V$s constructed by 5 $V_H$s and 5 $V_L$s were analyzed by SEC-HPLC, and the results of the analysis are shown in FIG. 21.

Figure 22:
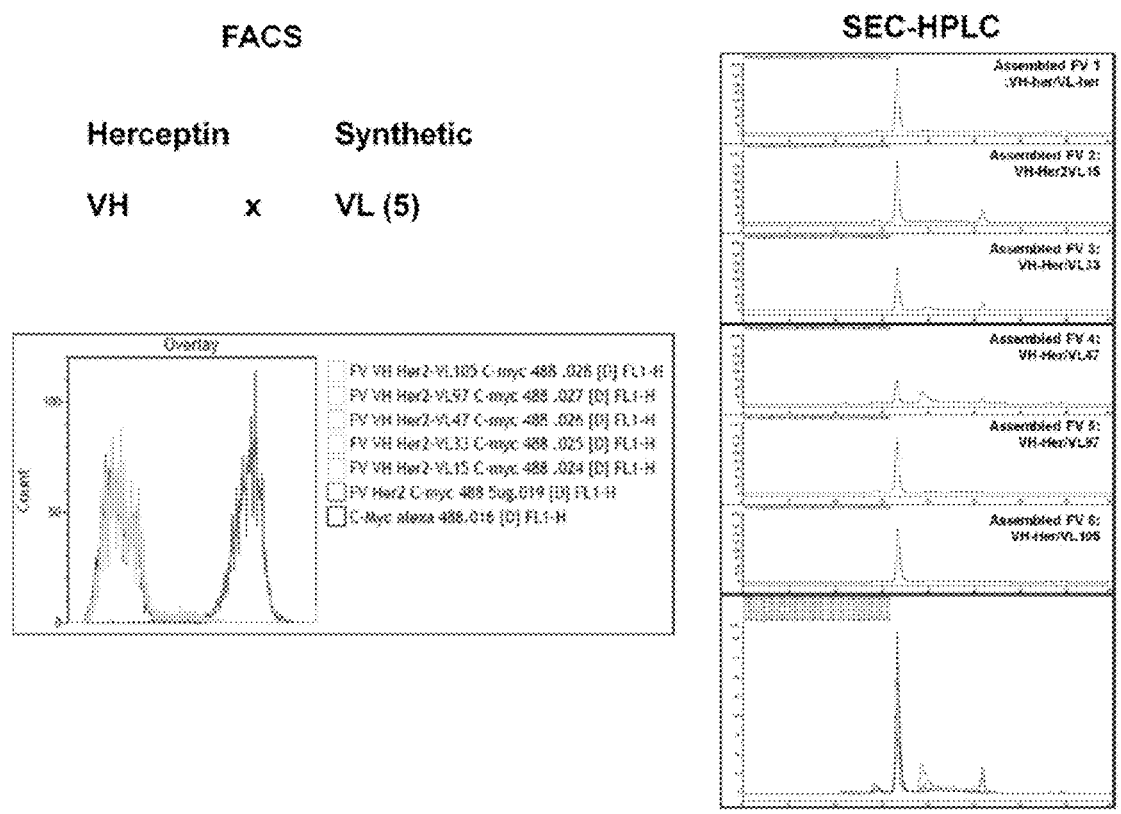
FIG. 22 shows the results of FACS and SEC-HPLC analysis of assembled $F_V$s prepared by combining 4D5 $V_H$ with 5 synthetic $V_L$s.

A combination of 4D5 $V_H$ and five synthetic $V_L$s was analyzed by FACS and SEC-HPLC, and the results of the analysis are shown in FIG. 22. Assembled $F_V$s constructed by the combination of 4D5 $V_H$ and five synthetic $V_L$s were analyzed by SEC-HPLC. However, it was shown that the assembled $F_V$s did not bind to BT-474 cells.

Experimental Example 9: Library Screening

For library screening, 10 antigens, including Fc-conjugated CTLA4, 41BB, TRAL R1, cMET, TRALI R2, CD40, Frizzled receptor 7, CD30, IL-17R and CSF1-R, were selected. In a first screening step, the interaction of individual $F_V$ with 10 mixed antigens was analyzed by alpha assay Amplified Luminescent Proximity Homogeneous Assay), and in a second screening step, the interaction of selected antibodies with individual antigens was screened. The library screening process is shown in FIG. 23.

The alpha assay is a bead-based proximity assay of donor beads and acceptor beads. In this assay, biotinylated antigens can be captured with streptavidin-coated beads, and myc-tagged $F_v$ can bind to anti-myc-conjugated acceptor beads. The donor bead and the acceptor bead become proximal to each other by antigen-$F_v$ interactions. The donor bead is excited at 680 nm as a result of the emission of singlet oxygen, and a fluorescence signal amplified by singlet oxygen is emitted from the acceptor bead to detect an alpha signal.

Figure 24:
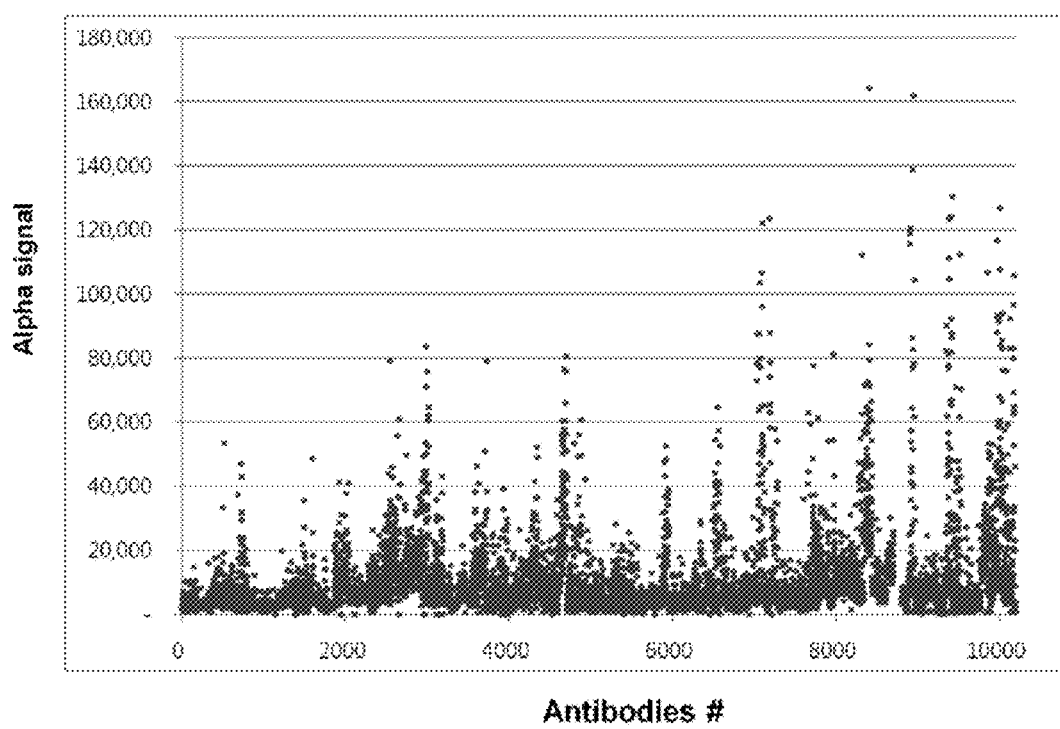
FIG. 24 shows the results of screening the interactions between individual Fvs and 10 mixed antigen by alpha assay.

FIG. 24 shows the results of screening the interaction of individual $F_v$s with 10 mixed antigens by the alpha assay. In FIG. 24, the Y-axis indicates the alpha signal, and the X-axis indicates 10000 screened $F_v$s. As can be seen therein, various antibodies in the range from high signals to low signals close to the background were screened.

Figure 25:
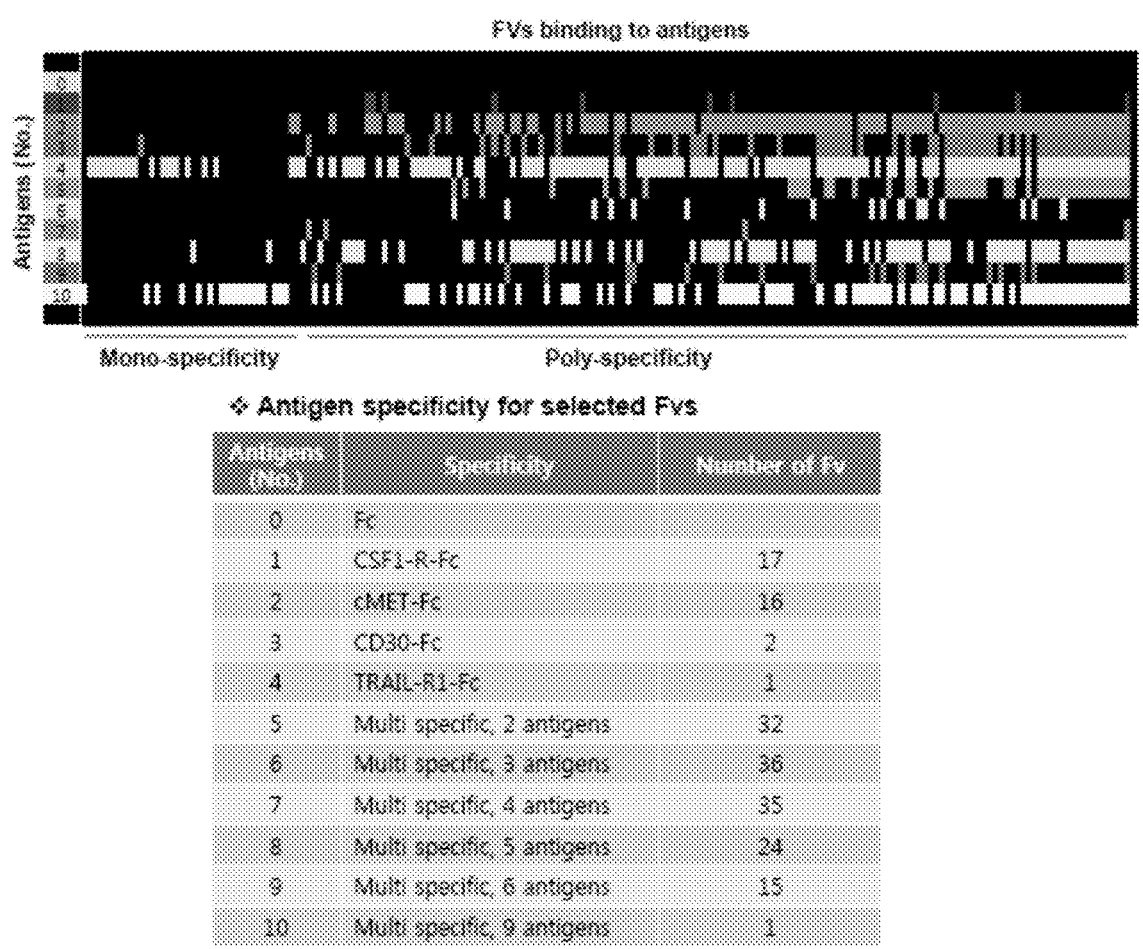
FIG. 25 shows the results of screening the interactions between Fvs binding to mixed antigens and individual antigens in a second screening step.

In a second screening step, the interaction between $F_v$s binding to the mixed antigens and individual antigens was screened, and the results of the screening are shown in FIG. 25. Antibodies showing specificity for CSF1R, MET, CD30 and TRAIL-R1 could be found, and antibodies having multi-specificity for a combination of various antigens could be found.

Figure 26:
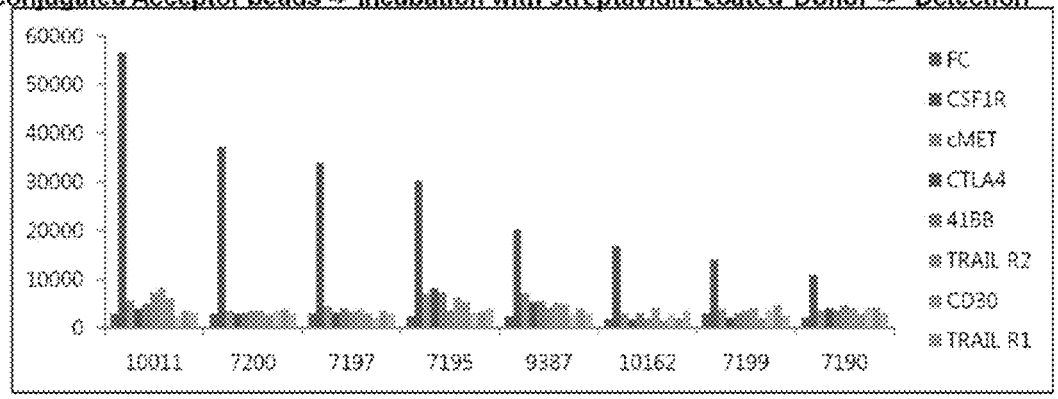
FIG. 26 is a graph showing the results of alpha assay for Fvs that bind mainly to CSF1R.
Figure 27:
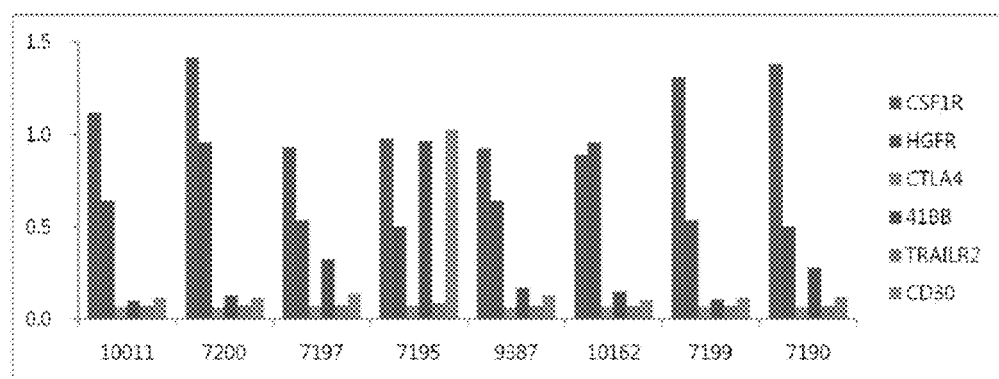
FIG. 27 shows the results of ELISA for the interaction of Fvs confirmed to bind mainly to CSF1R in alpha assay.

FIG. 26 shows the results of an alpha assay for Fvs binding mainly to CSF1R. In FIG. 26, various antibodies showing a difference in alpha signals can be seen. The interaction of Fvs binding mainly to CSF1R in the alpha assay was analyzed by ELISA, and the results of the analysis are shown in FIG. 27. It was shown that most of the Fvs did bind to both CSF1R and c-MET(HGFR). In addition, some Fvs, including Fv #7197 and #7195, showed multi-specificity.

Figure 28:
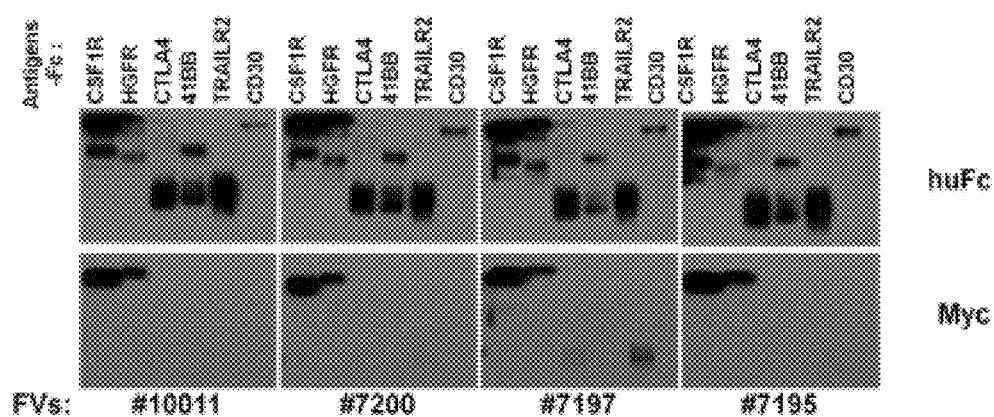
FIG. 28 shows the results of Western blotting for the interaction of Fvs confirmed to bind mainly to CSF1R in alpha assay.

The interaction of Fvs confirmed to bind mainly to CSF1R in the alpha assay was analyzed by Western blotting, and the results of the analysis are shown in FIG. 28. It was shown that most of the Fvs did bind to both CSF1R and c-MET(HGFR).

Figure 29:
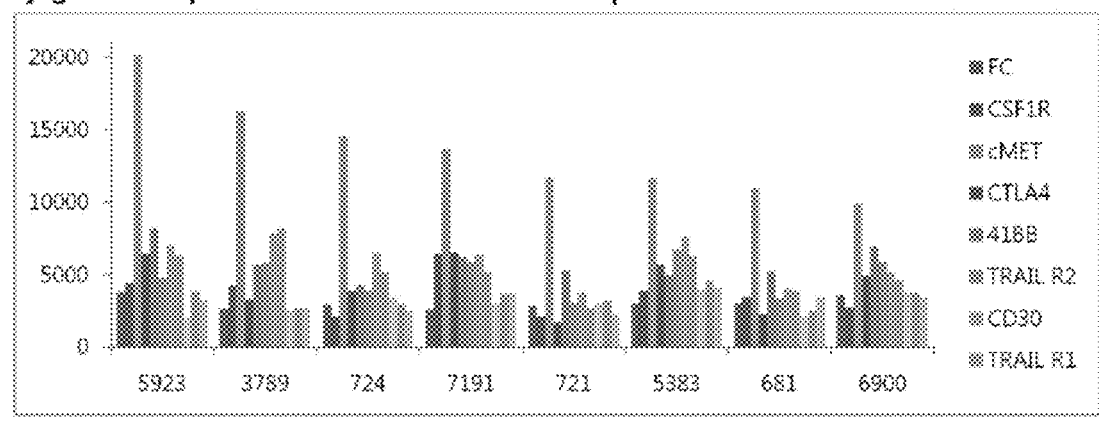
FIG. 29 is a graph showing the results of alpha assay for Fvs that bind mainly to c-MET.

FIG. 29 shows the results of an alpha assay for Fvs binding to c-MET. In FIG. 29, various antibodies showing a difference in alpha signals can be seen.

Figure 30:
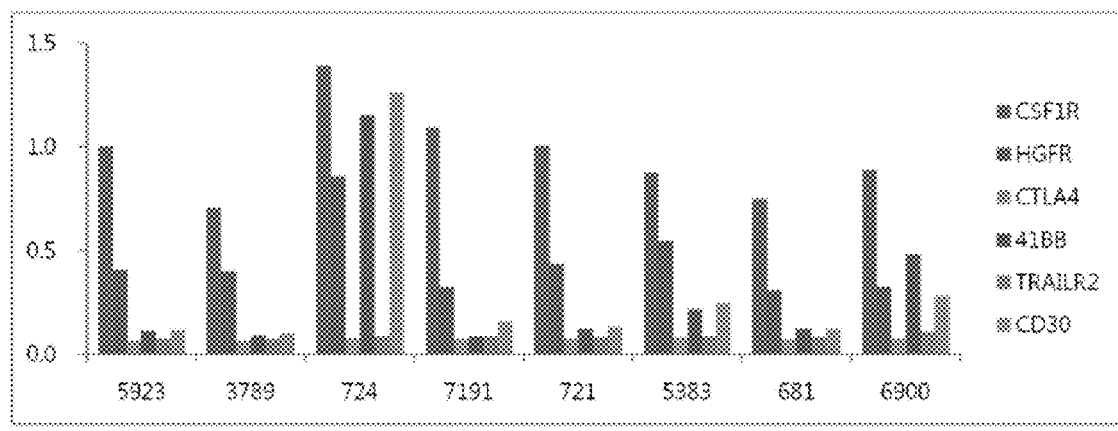
FIG. 30 shows the results of ELISA for the interaction of Fvs confirmed to bind mainly to c-MET in alpha assay.

The interaction of Fvs confirmed to bind mainly to c-MET in the alpha assay was analyzed by ELISA, and the results of the analysis are shown in FIG. 30. It was shown that most of the identified Fvs did bind to both CSF1R and c-MET (HGFR). In addition, some Fvs, including Fv #724 and #6900, showed multi-specificity.

Figure 31:
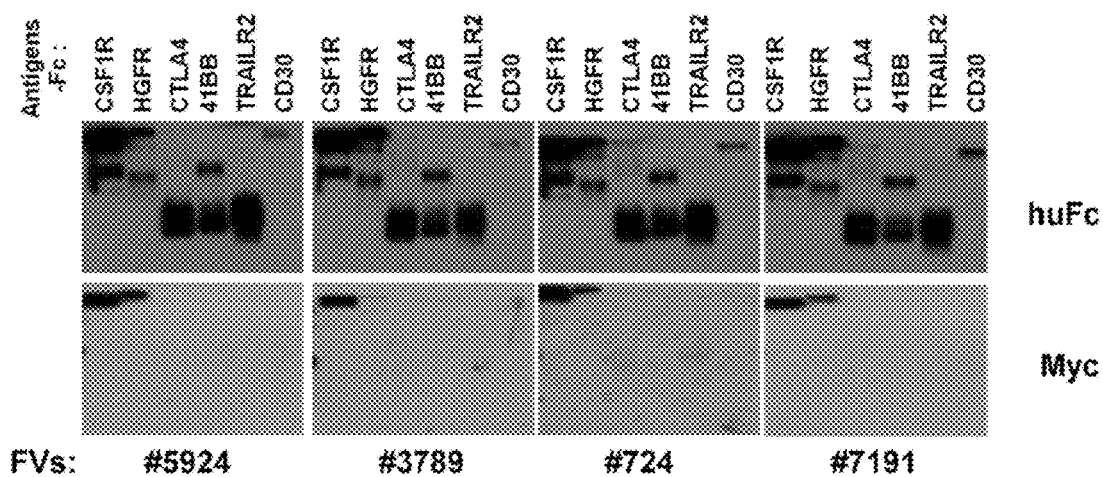
FIG. 31 shows the results of Western blotting for the interaction of Fvs confirmed to bind mainly to c-MET in alpha assay.

The interaction of Fvs confirmed to bind mainly to c-MET in the alpha assay was analyzed by Western blotting, and the results of the analysis are shown in FIG. 31. As can be seen in FIG. 31, most of the Fvs did bind to both CSF1R and c-MET(HGFR).

From the foregoing, it will be understood by those skilled in the art to which the present invention pertains that the present invention can be carried out in other concrete embodiments without changing the technical spirit or essential feature thereof. In this regard, it should be understood that the aforementioned examples are of illustrative in all aspects but not is limited. The scope of the present invention should be construed to include the meaning and scope of the appended claims, and all the alterations and modified forms which are derived from the equivalent concept thereof, rather than the detailed description.

INDUSTRIAL APPLICABILITY

The present invention is a platform for the construction of a novel Fv library. More specifically, the present invention can provide a platform for generation of novel antibodies, which can significantly reduce the time and cost required for purification and screening by combining $V_H$ and $V_L$ at the protein level, unlike conventional methods of combining antibody domains at DNA levels.

Due to such technical characteristics, therapeutic antibodies having practical function can be screened within a significantly short time at significantly reduced costs compared to conventional methods, and inhibitors, regulators and the like can also be developed without limitation on their targets.

In addition, the library of the present invention has no toxicity problem, unlike conventional libraries, and thus the function thereof can be immediately analyzed so that antibodies having various functions can be screened. In addition, the library of the present invention enables to screen functional antibodies that are involved in cell proliferation, differentiation, cell death or the like, or makes it possible to discriminate between normal and abnormal (target disease, phenomenon or condition) cells or individuals using antibodies. In other words, the library of the present invention can be applied for the production of antibody drugs, and can also be used in various applications, including the diagnosis of various diseases, the analysis of differentiation ability of stem cells, the stimulation of differentiation of stem cells, studies on disease mechanisms, antibody screening, the development of inhibitors and regulators, and antibody mapping (finger-printing) for various conditions (differentiation and undifferentiation, a disease group and a normal group).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for constructing an Fv library comprising:
   (a) expressing and purifying individual heavy-chain variable region ($V_H$) domain proteins from cells;
   (b) expressing and purifying light-chain variable region ($V_L$) domain proteins from cells separate from the cells in (a); and
   (c) pairing the purified VH domain proteins and the purified $V_L$ domain proteins to one another, wherein the $V_H$ domain proteins are fusion proteins, wherein the VL domain proteins are fusion proteins, and wherein $V_H$ domain proteins derive from the same $V_H$ domain and a mutation is introduced into the $V_H$ domain proteins such that the $V_H$ domain proteins comprise amino acid sequences that differ from each other; or wherein $V_L$ domain proteins derive from the same $V_L$ domain and a mutation is introduced into the $V_L$ domain proteins such that the $V_L$ domain proteins comprise amino acid sequences that differ from each other.

2. A method for constructing an Fv library comprising:
   (a) expressing and purifying individual heavy-chain variable region ($V_H$) domain proteins from cells;
   (b) expressing and purifying light-chain variable region ($V_L$) domain proteins from cells separate from the cells in (a); and
   (c) pairing the purified $V_H$ domain proteins and the purified $V_L$ domain proteins to one another, wherein the $V_H$ domain proteins are fusion proteins, wherein the $V_L$ domain proteins are fusion proteins, and wherein $V_H$ domain proteins derive from the same $V_H$ domain and a mutation is introduced into the $V_H$ domain proteins such that the $V_H$ domain proteins comprise amino acid sequences that differ from each other; and wherein $V_L$ domain proteins derive from the same $V_L$ domain and a mutation is introduced into the $V_L$ domain proteins such that the $V_L$ domain proteins comprise amino acid sequences that differ from each other.

3. The method of claim 1, wherein the $V_H$ domain proteins comprise complementarity determining regions (CDRs) and framework regions (FRs) and the $V_L$ domain proteins comprise complementarity determining regions (CDRs) and framework regions (FRs).

4. The method of claim 3 wherein CDRs of the $V_H$ domain proteins comprise amino acid sequences that differ from each other; CDRs of the $V_L$ domain proteins comprise amino acid sequences that differ from each other; FRs of the $V_H$ domain proteins comprise amino acid sequences that differ from each other; or FRs of the $V_L$ domain proteins comprise amino acid sequences that differ from each other.

5. The method of claim 4, wherein CDRs of the $V_H$ domain proteins comprise amino acid sequences that differ from each other; and CDRs of the $V_L$ domain proteins comprise amino acid sequences that differ from each other.

6. The method of claim 4 wherein FRs of the $V_H$ domain proteins comprise amino acid sequences that differ from each other; and FRs of the $V_L$ domain proteins comprise amino acid sequences that differ from each other.

7. The method of claim 5 wherein FRs of the $V_H$ domain proteins comprise amino acid sequences that differ from each other; and FRs of the $V_L$ domain proteins comprise amino acid sequences that differ from each other.

8. The method of claim 1, wherein step (c) comprises pairing the $V_H$ domain proteins and the $V_L$ domain proteins by random pairing or target pairing.

9. The method of claim 1, wherein the pairing of the $V_H$ domain proteins with the $V_L$ domain proteins in step (c) is performed by a method comprising: (i) pairing between wild-type $V_H$ domain proteins and the $V_L$ domain proteins; (ii) pairing by disulfide bonds between cysteine residues introduced into each of the $V_H$ domain proteins and the $V_L$ domain proteins; (iii) pairing by coiled-coil domains introduced into each of the $V_H$ domain proteins and the $V_L$ domain proteins; or (iv) pairing by protein-protein interaction between each of the $V_H$ domain proteins and the $V_L$ domain proteins.

10. A method for constructing an Fv library comprising:
    (a) expressing and purifying individual heavy-chain variable region ($V_H$) domain proteins from cells;
    (b) expressing and purifying light-chain variable region ($V_L$) domain proteins from cells separate from the cells in (a);
    (c) pairing the purified $V_H$ domain proteins and the purified $V_L$ domain proteins to one another; and
    (d) storing the paired $V_H$ domain proteins and $V_L$ domain proteins of step (c) in individual compartments, wherein the $V_H$ domain proteins are fusion proteins, wherein the VL domain proteins are fusion proteins, and wherein the individual compartments are assigned a unique identification (ID) number, and wherein the compartments comprise plate wells, test tubes, microfluidic channels, or chips.

11. The method of claim 10, wherein the $V_H$ domain proteins comprise complementarity determining regions (CDRs) and framework regions (FRs) and the $V_L$ domain proteins comprise complementarity determining regions (CDRs) and framework regions (FRs).

12. The method of claim 11, wherein CDRs of the $V_H$ domain proteins comprise amino acid sequences that differ from each other; CDRs of the $V_L$ domain proteins comprise amino acid sequences that differ from each other; FRs of the $V_H$ domain proteins comprise amino acid sequences that differ from each other; or FRs of the $V_L$ domain proteins comprise amino acid sequences that differ from each other.

13. The method of claim 12, wherein CDRs of the $V_H$ domain proteins comprise amino acid sequences that differ from each other; and CDRs of the $V_L$ domain proteins comprise amino acid sequences that differ from each other.

14. The method of claim 12, wherein FRs of the $V_H$ domain proteins comprise amino acid sequences that differ from each other; and FRs of the $V_L$ domain proteins comprise amino acid sequences that differ from each other.

15. The method of claim 13, wherein FRs of the $V_H$ domain proteins comprise amino acid sequences that differ from each other; and FRs of the $V_L$ domain proteins comprise amino acid sequences that differ from each other.

16. The method of claim 2, wherein step (c) comprises pairing the $V_H$ domain proteins and the $V_L$ domain proteins by random pairing or target pairing.

17. The method of claim 2, wherein the pairing of the $V_H$ domain proteins with the $V_L$ domain proteins in step (c) is performed by a method comprising: (i) pairing between wild-type $V_H$ domain proteins and the $V_L$ domain proteins; (ii) pairing by disulfide bonds between cysteine residues introduced into each of the $V_H$ domain proteins and the $V_L$ domain proteins; (iii) pairing by coiled-coil domains introduced into each of the $V_H$ domain proteins and the $V_L$ domain proteins; or (iv) pairing by protein-protein interaction between each of the $V_H$ domain proteins and the $V_L$ domain proteins.

\* \* \* \* \*